(12) United States Patent
Jimenez et al.

(10) Patent No.: US 8,728,442 B2
(45) Date of Patent: May 20, 2014

(54) METHOD OF CONTROLLING THE GROWTH OF MICROORGANISMS BY A COMPOSITION CONTAINING ISOLATED OR IN VITRO SYNTHESIZED NITROSOAMIDES

(75) Inventors: Jorge I. Jimenez, Sacramento, CA (US); Jonathan S. Margolis, Davis, CA (US); John Kenneth Baird, Davis, CA (US); Sarah F. Lego, Sacramento, CA (US)

(73) Assignee: Bayer CropScience LP, Research Triangle Park, NC (US)

( * ) Notice: Subject to any disclaimer, the term of this patent is extended or adjusted under 35 U.S.C. 154(b) by 0 days.

(21) Appl. No.: 13/319,870

(22) PCT Filed: May 11, 2010

(86) PCT No.: PCT/US2010/034456
§ 371 (c)(1),
(2), (4) Date: Nov. 10, 2011

(87) PCT Pub. No.: WO2010/132509
PCT Pub. Date: Nov. 18, 2010

(65) Prior Publication Data
US 2012/0058058 A1 Mar. 8, 2012

Related U.S. Application Data

(60) Provisional application No. 61/177,249, filed on May 11, 2009, provisional application No. 61/294,399, filed on Jan. 12, 2010, provisional application No. 61/227,051, filed on Jul. 20, 2009.

(51) Int. Cl.
*A01N 25/12* (2006.01)
*A01N 63/00* (2006.01)

(52) U.S. Cl.
CPC ...................................... *A01N 63/00* (2013.01)
USPC ............................................ 424/45; 514/482

(58) Field of Classification Search
CPC ...................................................... A01N 63/04
USPC ...................... 424/45, 93.5; 514/482; 435/254
See application file for complete search history.

(56) References Cited

U.S. PATENT DOCUMENTS

| | | | | |
|---|---|---|---|---|
| 3,009,854 A * | 11/1961 | Russell | ........................ | 514/482 |
| 4,283,408 A | 8/1981 | Hirata et al. | | |
| 6,911,338 B2 * | 6/2005 | Strobel et al. | ............... | 435/254.1 |
| 7,754,203 B2 | 7/2010 | Strobel et al. | | |
| 8,093,024 B2 | 1/2012 | Strobel et al. | | |
| 2004/0141955 A1 | 7/2004 | Strobel et al. | | |

FOREIGN PATENT DOCUMENTS

| | | |
|---|---|---|
| JP | 55-102548 | 8/1980 |
| WO | 02/06354 A1 | 1/2002 |

OTHER PUBLICATIONS

Zyryanov et al; "Encapsulted Reagents for Nitrosation"; published Mar. 15, 2003, Organic letters 5(8), 2003, p. 1253-1256; American Chemical Society.*

Ezra, D., et al., "New Endophytic Isolates of *Muscodor albus*, a Volatile-Antibiotic-Producing Fungus," Microbiology, vol. 150, pp. 4023-4031, 2004.

Ezra, D. & Strobel, G.A., "Effect of Substrate on the Bioactivity of Volatile Antimicrobials Produced by *Muscodor albus*," Plant Sci, vol. 165, pp. 1229-1238, 2003.

Qianhuan, D., et al., "Pattern Recognition Data for Structure—Carcinogenic Activity Relationship of N-Nitroso Compounds Based Upon Di-Region Theory," Huanjing Huaxue (Environmental Chemistry), vol. 6, No. 6. pp. 1-12, 1987.

Strobel, G., "*Muscodor* Species—Endophytes with Biological Promise," Phytochemlstry Reviews, vol. 10, No. 2, pp. 165-172, Feb. 6, 2010.

Zyranov, G.V., et al., "Sensing and Fixation of NO2/N2O4 by Calix[4]Arenes," Journal of the American Chemical Society, vol. 125, No. 10, pp. 2997-3007, 2003.

Zyranov, G.V. & Rudkevich, D.M., "Encapsulated Reagents for Nitrosation," Organic Letters, vol. 5, No. 8, pp. 1253-1256, 2003.

Djerassi, C., et al., "Optical Rotary Dispersion Studies. XLVIII. The Nitroso Chromophore," Journal of the American Chemical Society, vol. 83, pp. 2307-2312, 1961.

Neiswender, Jr., D.D. et al., "The Oxidation of Methylene Groups by Sodium Hypochlorite," Journal of the American Chemical Society, vol. 82, pp. 2876-2878, 1960.

Schwaier, R. & Zimmermann, F.K., "Chemical Constitution and Mutagenic Efficiency: Mutation Induction in *Saccharomyces cerevisiae* by a Homologous Series of N-Nitroso-N-Methylcarbonamides." Zeitschrift fuer Vererbungslehre, vol. 98, No. 4, pp. 309-319, 1966.

Brundrett, R.B., et al., "Comparison of Mutagenicity, Antitumor Activity, and Chemical Properties of Selected Nitrosoureas and Nitrosoamides," Cancer Research, vol. 39, No. 4, pp. 1328-1333, 1979.

Nikolaides, N., et al., "New Chemistry of Diazoesters from Thermal Rearrangement of N-alkyl-N-nitrosamides," Tetrahedron Letters, vol. 31, No. 42, pp. 6009-6012, 1990.

Godfrey, A.G. & Ganem, B., "New Syntheses of Alkenes and Alkynes from Amines," Journal of the American Chemical Society, vol. 112, No. 9, pp. 3717-3718, 1990.

Saavedra, J.E., "Reduction of Nitrosoamides to Alcohols Using Sodium Borohydride," Journal of Organic Chemistry, vol. 44, No. 5, pp. 860-861, 1979.

Berenguer, R., et al., "Conversion of Amides to S-Alkyl and S-Aryl Thioesters via Nitrosoamides and Nitroamides," Synthesis, vol. 4, pp. 305-306, 1989.

Garcia, J. & Vilarrasa, J., "New Synthetic 'Tricks' from Aliphatic Amines and Amides to Azides and/or How to Convert RNHCOR' into RNHCOR" Avoiding Drastic Hydrolyses," Tetrahedron Letters, vol. 28, No. 3, pp. 341-342, 1987.

(Continued)

*Primary Examiner* — Richard Schnizer
*Assistant Examiner* — Yanzhi Zhang
(74) *Attorney, Agent, or Firm* — Michelle L. Samonek

(57) ABSTRACT

The present invention relates to novel compounds and compositions and the use of them for the control of fungal and bacterial pathogens, insect pests, acari, nematodes and other invertebrate pests including, but not limited to post-harvest and soil diseases, building mold remediation, and seed and grain sanitation.

11 Claims, 15 Drawing Sheets

(56) References Cited

OTHER PUBLICATIONS

Garcia, J., et al., "Reaction of N-Nitroso- and N-Nitro-N-alkylamides with Amines," Journal of Organic Chemistry, vol. 49, No. 18, pp. 3322-3327, 1984.

Cooper, C.N., et al., "Classical Carbonium Ions. Part 13. Rearrangements from Secondary to Primary Alkyl Groups during Reactions involving Carbonium Ions," Journal of the Chemical Society, Perkin Transactions II (1972-1999), vol. 5, pp. 605-611, 1982.

Heydt, H., "Product Class 21: Diazo Compounds," in Science of Synthesis, vol. 27, pp. 843-935, 2004.

Masui, M., et al., "Electrochemical Oxidation of N-Nitrosodialkylamines: Mechanism of N-Nitramine and beta-Ketonitrosamine Formation," Chemical & Pharmaceutical Bulletin, vol. 33, No. 7, pp. 2721-2730, 1985.

Fooladi, M.H., et al., "An Investigation into the Potential Formation of N-Substituted Amides and Their Nitrosated Derivatives during the Frying of Bacon," Journal of Agricultural and Food Chemistry, vol. 31, No. 3, pp. 527-530, 1983.

Moss, R.A. & Luchter, K.M., "The Acetylation of Butane 2-Diazotate. Mechanism of Decomposition of an Alkyl . Drazo Ester," Journal of Organic Chemistry, vol. 37, No. 8, pp. 1155-1161, 1972.

Friedman, L., et al., "Influence of Solvent on Diazoalkane-Alkyldiazonium Ion Equilibria in Amine Deaminations," Journal of the American Chemical Society, vol. 91, No. 7, pp. 1795-1799, 1969.

Maskill, H., et al., "Synchronous Fragmentation in the Deamination of Secondary Carbinylamines," Chemical Communications (London), vol. 20, pp. 496-498, 1965.

White, E.H., & Aufdermarsh, Jr., C.A., "N-Nitrosoamides. IV. N-Nitrosoamides of Primary Carbinamines," Journal of the American Chemical Society, vol. 83, No. 5, pp. 1174-1178, 1961.

Flesia, E., et al., "ESR Study of N-Acyl-N-Alkyl Nitroxide Radicals from Photolysis of N-Nitrosoamides," Organic Magnetic Resonance, vol. 11, No. 3, pp. 123-126, 1978.

Murakami, M., et al., "Effect of Hyperconjugation on the Decomposition of N-Alkyl-N-Nitrosoacetamide," Bulletin of the Chemical Society of Japan, vol. 35, No. 1, pp. 11-15, 1962.

Lijinsky, W. & Andrews, A.W., "The Mutagenicity of Nitrosamides in *Salmonella typhimurium*," Mutation Research/Genetic Toxicology, vol. 68, No. 1, pp. 1-8, 1979.

Zimmermann, F.K., et al., "Mitotic Recombination Induced in *Saccharomyces cerevisiae* with Nitrous Acid, Diethylsulfate and Carcinogenic, Alkylating Nitrosamides," Zeitschrift fuer Verenbungslehre, vol. 98, No. 3, pp. 230-246, 1966.

Lijinsky, W., et al., "Carcinogenesis in Rats by Substituted Dialkylnitrosamines Given by Gavage," In Vivo, vol. 5, pp. 85-90, 1991.

International Search Report and Written Opinion of the International Searching Authority, International Patent Application PCT/US10/34456, mailed Jul. 27, 2011, and Nov. 11, 2011, respectively.

\* cited by examiner

METHOD OF CONTROLLING THE GROWTH OF MICROORGANISMS BY A COMPOSITION CONTAINING ISOLATED OR IN VITRO SYNTHESIZED NITROSOAMIDES

RELATED APPLICATIONS

This application claims the benefit of U.S. Provisional Application No. 61/177,249, filed on May 11, 2009, U.S. Provisional Application No. 61/227,051, filed Jul. 20, 2009, and U.S. Provisional Application No. 61/294,399, filed Jan. 12, 2010, each of which are incorporated by reference in their entirety.

BACKGROUND OF THE INVENTION

Fumigants are among the most toxic and environmentally damaging pesticides still in wide use. Methyl bromide for example has been banned for its ozone depleting action. The continued use of these products reflects their unique ability to penetrate through a large volume of soil, structure, or agricultural commodity and then subsequently dissipate with no residue. The relatively unusual physical properties required for such products (high vapor pressure, non-flammable, non-reactive) have dramatically limited the number of options for fumigants. Most fumigants are extremely toxic and have non-specific modes of action. The discovery of *Muscodor albus*, an endophytic tropical fungus producing a highly potent biocidal mixture of volatile compounds, provided a natural product chemistry solution as an alternative to current fumigants. Natural products are often perceived to offer greater safety as well as lower environmental impact such that a biologically-derived fumigant would have great appeal to consumers. In addition, such product could serve the unmet need for fumigation in the organic food industry.

Previous publications regarding *Muscodor albus* note that no individual compound or class of compounds is lethal to any test microbes consisting of plant pathogenic fungi. A recent review of the *Muscodor* species states: "Obviously, the antibiotic effect of the VOCs of *M. albus* is strictly related to the synergistic activity of the compounds in the gas phase." See Strobel, G., *Phytochem. Rev.* published online Feb. 16, 2010. As noted, the active substances of *Muscodor albus* have not previously been defined and therefore synthetic scale-up of a pesticide product derived from these substances was challenging. Described herein is a compound from *Muscodor albus* and a method for identifying the compound. Also described are compounds, compositions and kits that have similar structures or bioactivity to that of the active substances of *M. albus*. Methods of making the compounds described herein are also provided. The compounds and compositions described herein may be useful for control of fungal and bacterial pathogens, insect pests, acari, nematodes and other invertebrate pests, for example, for post-harvest and soil diseases, building mold remediation, and seed and grain sanitation. Also described are synthetic mixtures and kits comprising compounds herein that have similar efficacy to the *Muscodor albus* for treating disease.

SUMMARY OF THE INVENTION

Provided herein are synthetic compounds of Formula 2:

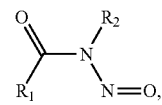

Formula 2 wherein $R_1$ and $R_2$ are each independently hydrogen or an alkyl, haloalkyl, cycloalkyl, or alkenyl group. In some embodiments, $R_1$ and $R_2$ are an alkyl group. In other embodiments, $R_1$ is a cycloalkyl group and $R_2$ is an alkyl group. In still other embodiments, $R_1$ is an alkene group and $R_2$ is an alkyl group.

Also provided herein are synthetic compounds of Formula 4:

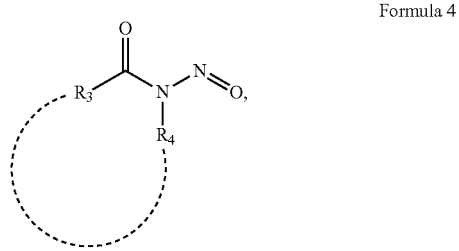

Formula 4 wherein $R_3$ and $R_4$ are attached to form a 4-, 5- or 6-membered substituted or unsubstituted heteroaryl or heterocycloalkyl group. In some embodiments, $R_3$ and $R_4$ form a 4-membered heterocycloalkyl group. In other embodiments, $R_3$ and $R_4$ form a 5-membered heterocycloalkyl group. In yet other embodiments, $R_3$ and $R_4$ form a 6-membered heterocycloalkyl group. In various embodiments, the compound of Formula 4 is selected from:

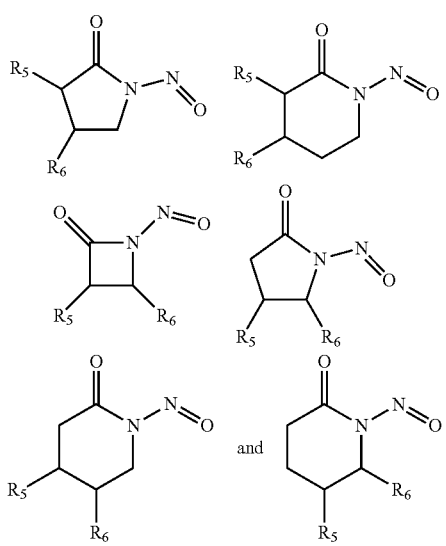

wherein $R_5$ and $R_6$ are attached to form a 3-, 4-, 5- or 6-membered substituted or unsubstituted aryl, heteroaryl, cycloalkyl or heterocycloalkyl group. In yet other embodiments, the compound of Formula 4 is selected from:

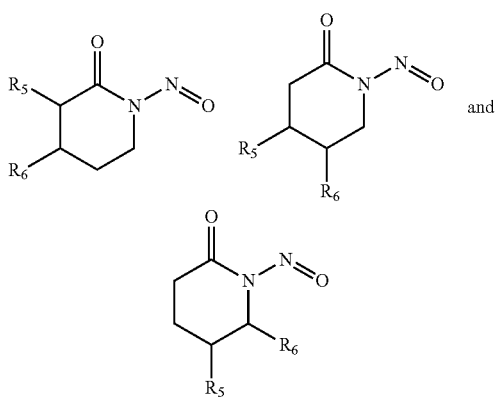

wherein $R_5$ and $R_6$ are attached to form a 3-, 4-, 5- or 6-membered substituted or unsubstituted aryl, heteroaryl, cycloalkyl or heterocycloalkyl group. In still other embodiments, the compound of Formula 4 is selected from:

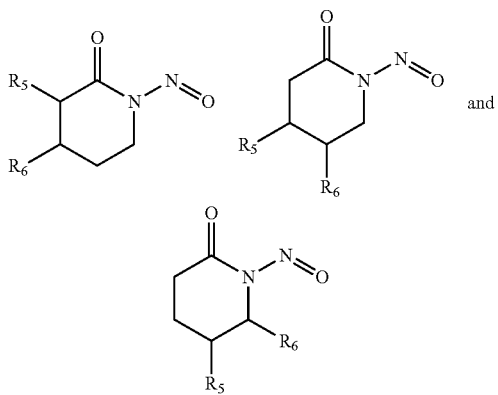

wherein $R_5$ and $R_6$ are each independently hydrogen or a substituted or unsubstituted alkyl, haloalkyl, cycloalkyl, or alkenyl group.

The compounds described above and herein may be produced by any means. They may be synthetically made, as described in the Examples and Detailed Description, or they may be isolated from a *Muscodor* fungus or some other microorganism that produces such compound(s). Isolation may occur according to the methods described herein, such as in Example 2. Compounds isolated from a microorganism or made synthetically may be at least about 80% pure, at least about 85% pure, at least about 90% pure, at least about 91% pure, at least about 92% pure, at least about 93% pure, at least about 94% pure, at least about 95% pure, at least about 96% pure, at least about 97% pure, at least about 98% pure, or at least about 99% pure. In another embodiment the compounds described above are produced by a microorganism other than *Muscodor* that is isolated from nature. Such non-*Muscodor* produced compounds may or may not be purified from the isolated microorganism.

Also provided herein are prodrugs of compounds of Formula 2 and Formula 4. As recognized by those of skill in the art, the term "prodrug" refers to compounds that are transformed in vivo to yield the parent compounds described herein. A discussion of prodrugs is provided in T. Higuchi and V. Stella, Prodrugs as Novel Delivery Systems (1987) 14 of the A.C.S. Symposium Series, and in Bioreversible Carriers in Drug Design, (1987) Edward B. Roche, ed., American Pharmaceutical Association and Pergamon Press, both of which are incorporated herein by reference thereto. In some embodiments, the prodrug is a molecule that is converted to a compound of Formula 2 or Formula 4 when mixed with another reagent, including but not limited to an enzyme. In other embodiments, the prodrug is a molecule that is converted to a compound of Formula 2 or Formula 4 within an organism. In yet other embodiments, the prodrug is a molecule that is converted to a compound of Formula 2 or Formula 4 when exposed to water or light. In still other embodiments, the prodrug is a molecule that allows for the time release of a compound of Formula 2 or Formula 4.

In some embodiments, the compound of Formula 2 or Formula 4 is included in a kit or a composition and the kit or composition further comprises a delivery agent. In various embodiments, the compound is volatile and water soluble at ambient conditions. In some embodiments, the delivery agent is a liquid. In other embodiments, the liquid delivery agent comprises a propellant, a volatile liquid, or dip or coating for an object. In other embodiments, the delivery agent is liquid based fogging agent. In one embodiment, the composition or kit includes a delivery agent and a compound of Formula 2 or Formula 4, but excluding Compound 1, as described below.

In other embodiments, the delivery agent may be a solid. In some embodiments, the solid is a gel containing the compound. In still other embodiments, the delivery agent is a solid, such as a solid matrix. In some embodiments the solid matrix is film or tape. In other solid embodiments, the compound may be incorporated into a tape, film or package.

In other embodiments, the compound of Formula 2 or Formula 4 is included in a kit and the kit further comprises a delivery device. In some embodiments, the delivery device is an aerosol delivery device, or a drip irrigation system, or an injection device. In other embodiments, the delivery device comprises a pressurized container.

Provided herein in various embodiments are compounds capable of transforming into an alkylating species and/or nitrosylating species in a cell. In some embodiments, the compound is capable of forming diazoalkane in a cell.

Also provided herein are methods comprising the steps of: (a) growing *Muscodor*; (b) obtaining volatile gas from the *Muscodor* by contacting the volatile gas with a sorbent; (c) releasing the volatile gas from the sorbent with an eluant; and (d) identifying the volatile gas released from the sorbent. In some embodiments, the growing step comprises growing *Muscodor albus* on rye grain. In a specific embodiments, the growing step comprises growing *Muscodor albus* CZ620 (*cinnamomum zeylanicum*) on rye grain. In other specific embodiments, the growing step comprises growing *Muscodor albus* in a submerged fermentation or a solid state fermentation. In some embodiments, the eluant used in the method described herein is an alcohol or absolute ethanol. In some embodiments, the step of identifying in the methods described herein comprises conducting gas chromatography on the volatile gas. In some embodiments, the identifying further comprises conducting mass spectrometry on the volatile gas. In some embodiments, the gas chromatography and mass spectrometry are carried out at a temperature of less than 220° C.

Also provided herein are methods comprising the steps of: (a) obtaining volatile gas from a *Muscodor* fungus using a sorbent; (b) releasing the volatile gas from the sorbent with a solvent; and (c) collecting the volatile gas released from the sorbent.

In some embodiments, the obtaining step in the methods described here comprises obtaining the volatile gas from the headspace of a vessel containing either a solid state fermentation or a submerged fermentation of *Muscodor*. In some embodiments, the sorbent used in the methods described herein is selected from the group consisting of Amberlite XAD2, Amberlite XAD4, Amberlite XAD16, Diaion HP-20, Sepabeads SP-207, Dowex Optipore SD-2 and charcoal.

In specific embodiments described herein, the *Muscodor* is *Muscodor albus* or *Muscodor crispans*. See Mitchell et al., *Muscodor crispans, a novel endophyte from Ananas ananassoides in the Bolivian Amazon*, FUNGAL DIVERSITY (31 Jul. 2008) p. 37. In various embodiments, the strain of *Muscodor albus* is strain E6 (*guazuma ulmifolia*), or GP-100 (*grevillea pteridifolia*), or GP-206 (*grevillea pteridifolia*), or KN-205 (*kennedia nigriscans*), or KN-205 (*kennedia nigriscans*), or TP-21 (*terminalia prostrate*), or CZ620 (*cinnamomum zeylancicum*). See, e.g., David Ezra et al., *New endophytic isolates of Muscodor albus, a volatile-antibiotic-producing fungus*, 150 MICROBIOLOGY (2004) 4023-4031. In other embodiments, the *Muscodor* is *Muscodor crispans* and the strain is B-23 (*ananas ananassoides*).

Also provided here are methods of sanitizing materials. In some embodiments, the material is a foodstuff, such as a crop, a stored grain or a meat product. In other embodiments, the material is soil. In still other embodiments, the material is a building material, including wood and drywall, or an existing structure or part of an existing structure, such as a crawlspace or ventilation ducts.

Also provided herein are methods of sanitizing a household object comprising contacting the household object with a compound of Formula 2 or a compound of Formula 4. In some embodiments, the contacting step is carried out by fumigating the material.

Also provided herein are methods of sanitizing a building material comprising contacting the building material with a compound capable of transforming into a non-halogen alkylating agent. In some embodiments, the non-halogen alkylating agent is diazomethane. In some embodiments the method of sanitizing a building material comprises contacting the building material with a compound capable of forming diazoalkane.

Provided herein in various embodiments are methods of sanitizing a foodstuff comprising contacting the foodstuff with a compound capable of transforming into a non-halogen alkylating or nitrosylating species. In some embodiments, the non-halogen alkylating agent is diazomethane. In some embodiments, the method of sanitizing a foodstuff comprises contacting the foodstuff with a compound capable of forming diazomethane.

The invention further provides a composition comprising a compound of Formula 2 or Formula 4:

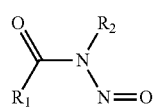

Formula 2

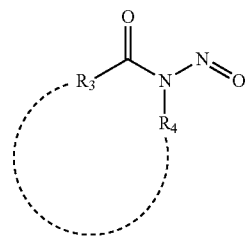

Formula 4 wherein $R_1$ and $R_2$ are each independently hydrogen or an alkyl, haloalkyl, cycloalkyl, or alkenyl group; $R_3$ and $R_4$ taken together form a 4-, 5- or 6-membered substituted or unsubstituted heteroaryl; and wherein the composition additionally comprises a delivery agent. In some embodiments, the delivery agent is, for example, a propellant or a gel. In some embodiments, the deliver agent is a liquid or a solid. In other embodiments, the delivery agent is a gas. In one embodiment, the delivery agent excludes agents suitable for administration to humans.

Provided herein is also a method of evaluating a compound for biocidal activity comprising: (a) providing a compound to be tested; (b) evaluating a biocidal property of said compound; and (c) comparing said biocidal property to the biocidal activity of a compound of the invention.

In certain specific embodiments of the invention described herein, the compound of Formula 2 is N-methyl N-nitrosoisobutyramide (Compound 1).

In other embodiments, this compound is of Formula 2:

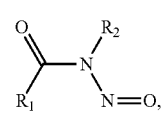

Formula 2 wherein $R_1$ and $R_2$ are each independently hydrogen or an unsubstituted alkyl or unsubstituted cycloalkyl, with the proviso that the following compounds are excluded:

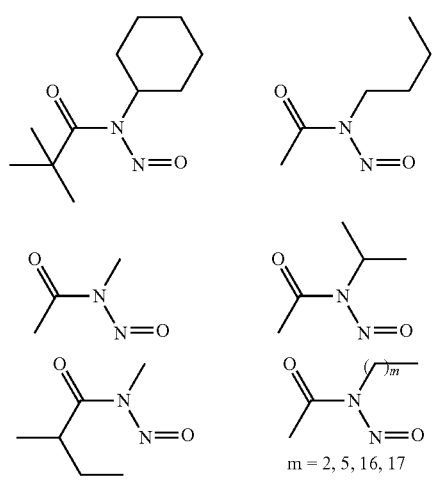

m = 2, 5, 16, 17

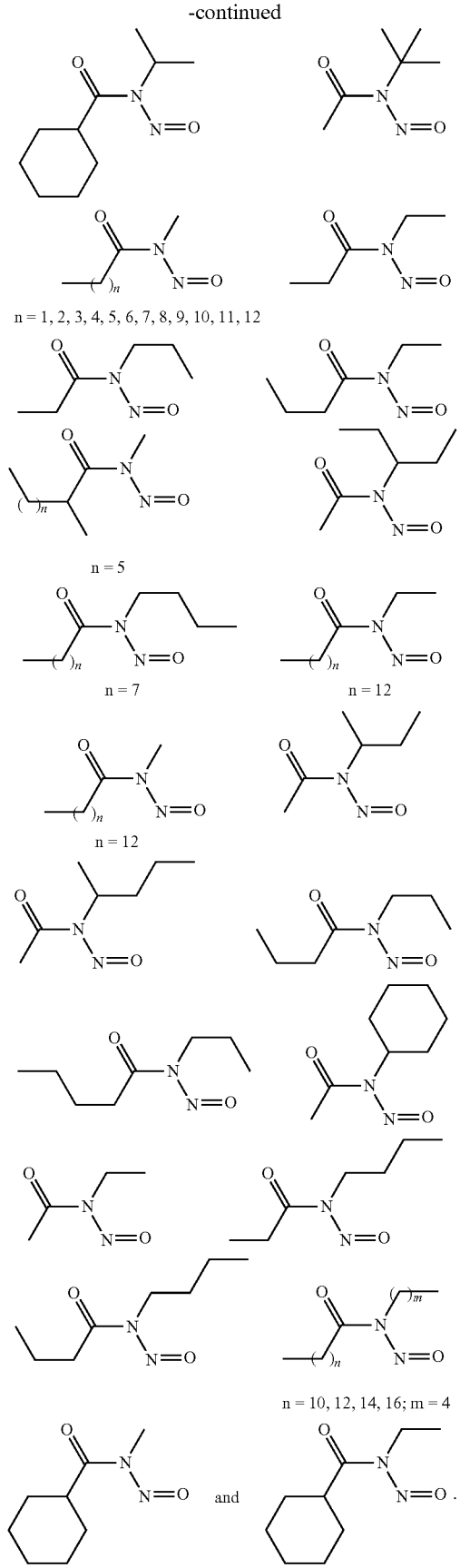

It should be noted that the above disclaimer of compounds does not apply to the descriptions below or to the claims, unless the disclaimer is explicitly made.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Many features herein are set forth with particularity in the appended claims. A better understanding of the features and advantages herein will be obtained by reference to the following detailed description that sets forth illustrative embodiments, in which many principles are utilized, and the accompanying drawings of which:

DETAILED DESCRIPTION OF THE INVENTION

Figure 1:
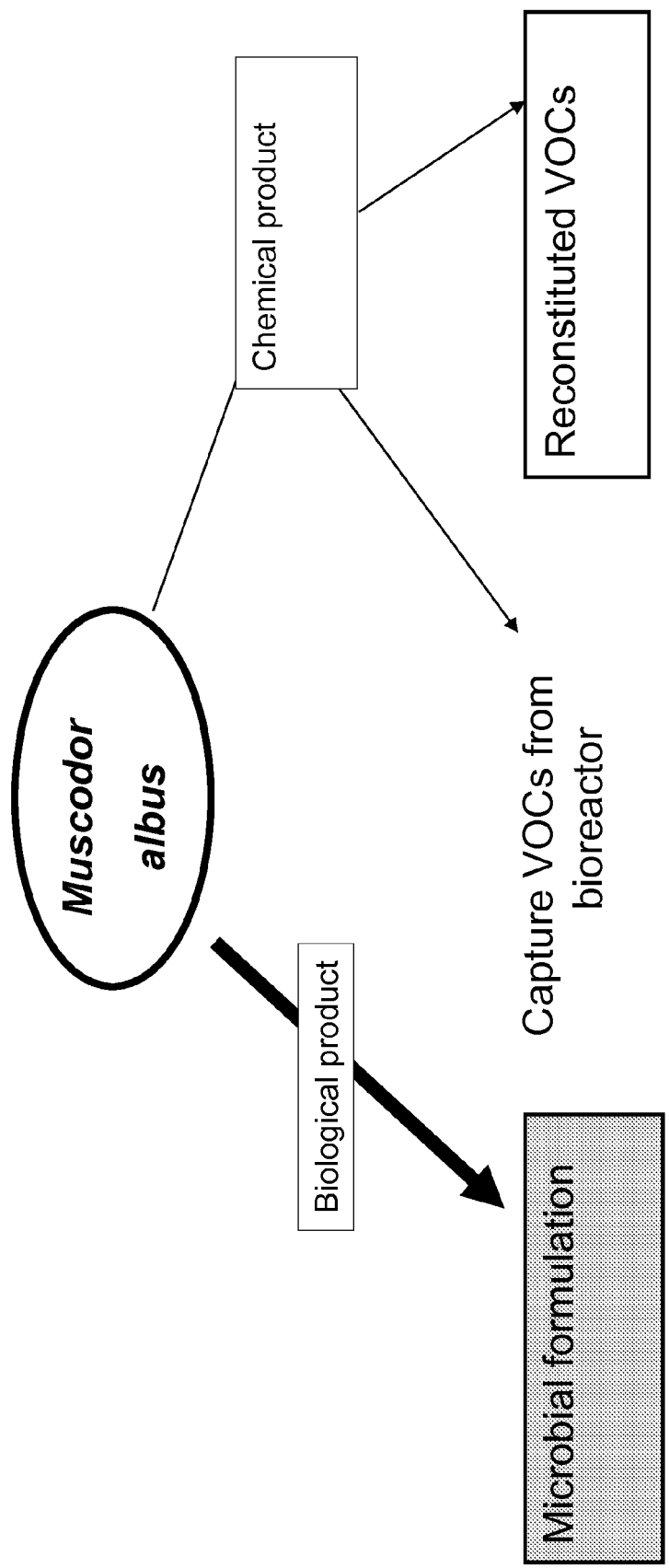
FIG. 1 illustrates products that are developed from *Muscodor albus*.
Figure 2:
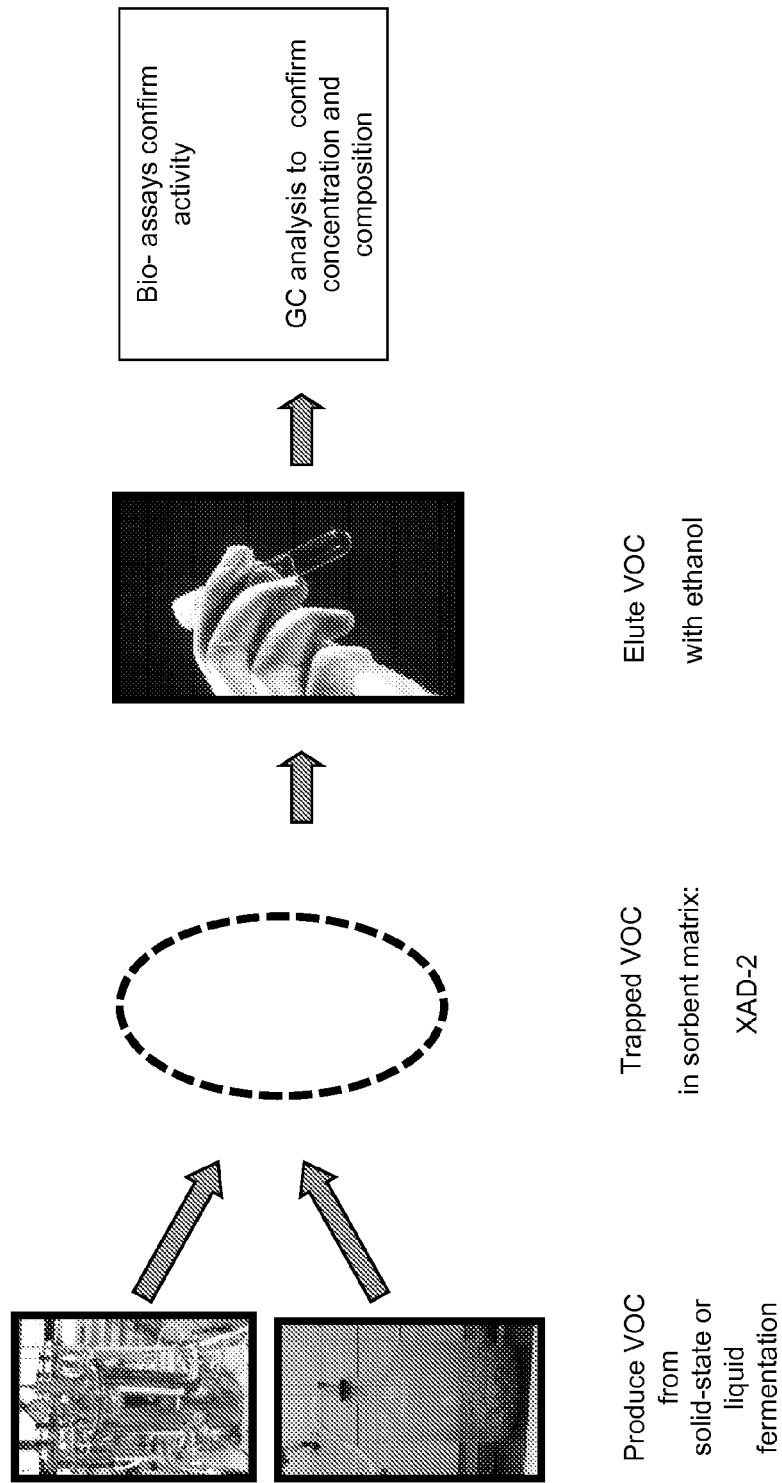
FIG. 2 illustrates a method herein of collecting VOCs from *Muscodor* by trapping the VOCs with a sorbent.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein are employed in practicing the invention. Many features herein are set forth with particularity in the appended claims. It is intended that the claims define the scope of the invention and that methods and structures within the scope of these claims and their equivalents be covered thereby.

A better understanding of the features and advantages of the present invention will be obtained by reference to the following detailed description that sets forth illustrative embodiments, in which many principles of the invention are utilized. The section headings used herein are for organizational purposes only and are not to be construed as limiting the subject matter described.

Methods of Isolating Compounds of the Present Invention from Muscodor

*Muscodor* is a genus of fungi in the Xylariaceae family noted for their ability to produce a variety of volatile organic compounds, which inhibit growth of other fungi. Known habitats of *Muscodor* species include Honduras, Venezuela, Thailand, and Australia's Northern Territory.

The first species to be identified was *Muscodor albus*, an endophytic fungus isolated from *cinnamomum zeylanicum* growing in a botanical garden in Honduras. The most notable property of the *Muscodor albus* organism was its ability to produce a mixture of volatile organic compounds (VOCs) that were lethal to a wide variety of human- and plant-pathogenic fungi and bacteria. Subsequently, other strains of *Muscodor albus* and other species of *Muscodor* were isolated, including *Muscodor roseus*, *Muscodor vitigenus*, and *Muscodor crispans*. Although these produced different collections of VOCs, all shared the property of producing VOCs which were potently anti-microbial.

The VOCs from the fungus consist primarily of various alcohols, acids, esters, ketones and lipids. Synthetic mixtures of the VOCs mimicked the biological effects of the fungal VOCs when tested against a wide range of fungal and bacterial pathogens but did not have the potency of the fungally-produced VOCs at a comparable concentration. In other words, such synthetic mixtures required much higher concentrations to achieve comparable efficacy.

As provided herein, VOCs produced by *Muscodor albus* can be trapped onto a sorbent, for example, a solid sorbent. Exemplary solid sorbents for use herein include, but are not limited to: Amberlite XAD2, Amberlite XAD4, Amberlite XAD16, Diaion HP-20, Sepabeads SP-207, Dowex Optipore SD-2 and charcoal. Other exemplary sorbents include those that are used for environmental chemistry studies, such as trapping of pollutants that are present in trace amounts. Other exemplary sorbents may have some properties in common, such as a matrix with a particle size of about 250-850 μm or about 18 to 50 or about 20 to 60 mesh, a pore size of about 50 Å or between about 40 to 260 Å or about 120 to 260 Å, and a pore volume of between about 0.4 to 2 mL/g or about 1.2 to 1.3 mL/g.

The absorbed VOCs can be released from the sorbent with a suitable solvent (for example, ethanol), and the ethanol eluate, which can be used as a composition herein. The composition can be used to control fungi, bacteria, insects, nematodes, acari and other invertebrate pests. In studies provided herein, the composition demonstrated the same level of efficacy against fungi and bacteria as the volatiles produced by the microbial formulation of the *Muscodor albus* on rye grain.

Figure 3:
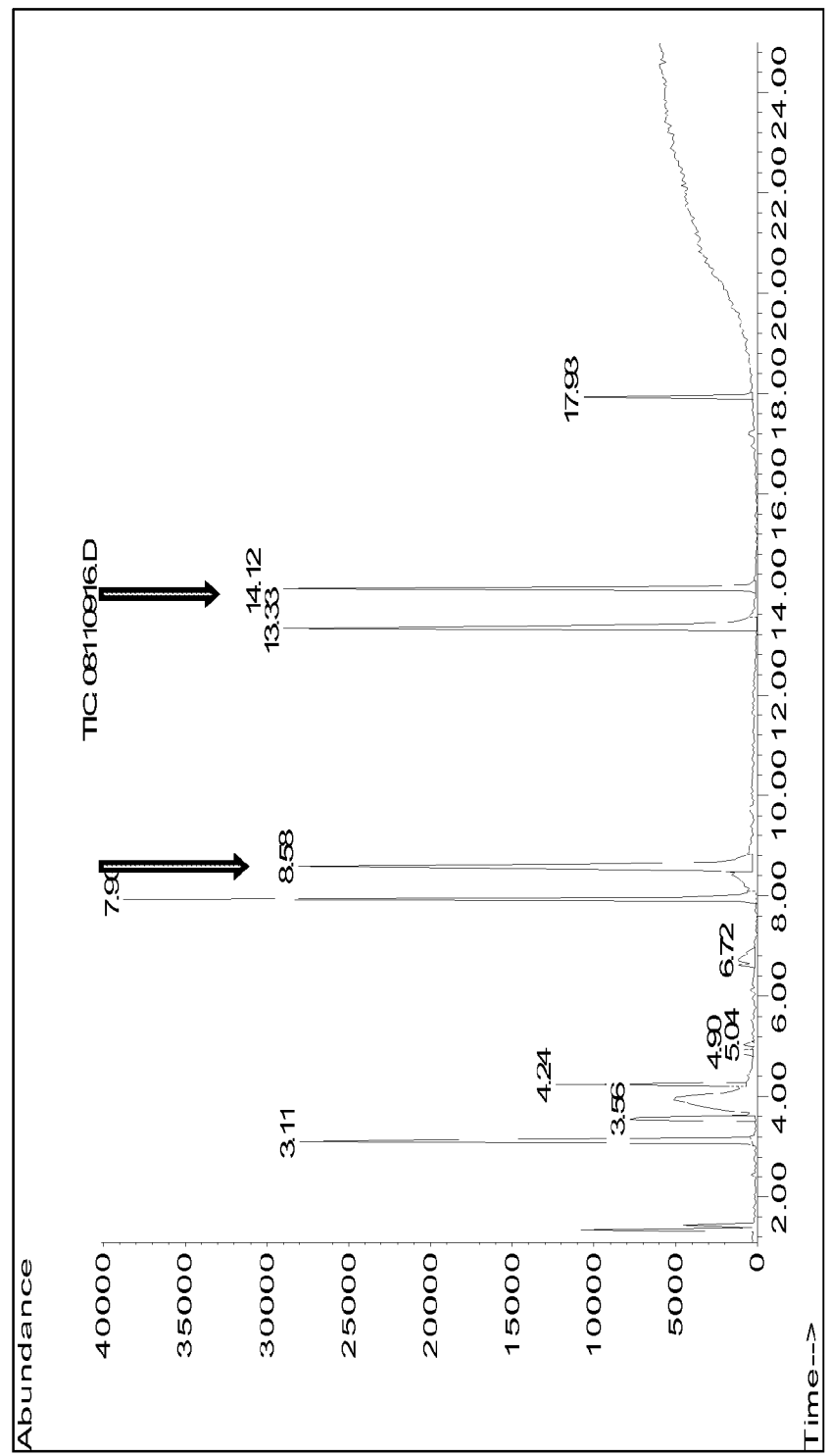
FIG. 3 illustrates an exemplary GC/MS profile of VOCs from *M. albus* as trapped by a sorbent and eluted by ethanol as described herein.

FIG. 3 illustrates a method herein of collecting VOCs from *Muscodor*. The fungi can be grown in a liquid fermentation or a solid state fermentation. The growing fungi produce VOCs in the headspace of the reactors that can be trapped in a sorbent (for example, XAD-2). The VOCs can then be eluted from the sorbent with an eluant, such as ethanol, and collected. After collection, the VOCs can be incorporated into a product, optionally after removing the eluant and/or concentrating the VOCs or, as shown in FIG. 3, can be tested in bio-assays to confirm activity or assayed by GC, GC/MS, or MS systems to confirm the composition and concentration of the VOCs.

Previously, it was postulated that VOCs responsible for the inhibitory activity of *Muscodor albus* were esters, alcohols and acids. Also it has been shown that new isolates of *Muscodor albus* make other VOCs such as naphthalene and an alcohol, an acid, and/or other naphthalene/azulene derivatives that possess biological activity both in vivo and in artificial mixtures. Before the work herein, it appeared that no individual compound by itself possessed major antifungal activity, nor was a combination of compounds sufficient to reproduce the native bioactivity at comparable concentration levels. As described herein, this is because prior to the methods described herein, the compositions described herein were not known. The compositions described herein can degrade at elevated temperatures, such as those temperatures at which compounds are injected into a gas chromatograph (GC). Previously, VOCs were identified from *Muscodor albus* by GC/MS at standard temperatures using collection and desorption from a polydimethyl siloxane matrix (PDMS) or direct analysis (funneling the microbially produced VOCs to the GC/MS directly without first collecting on a matrix) and other similar methods; therefore, the compositions described herein have never before been detected.

Figure 4:
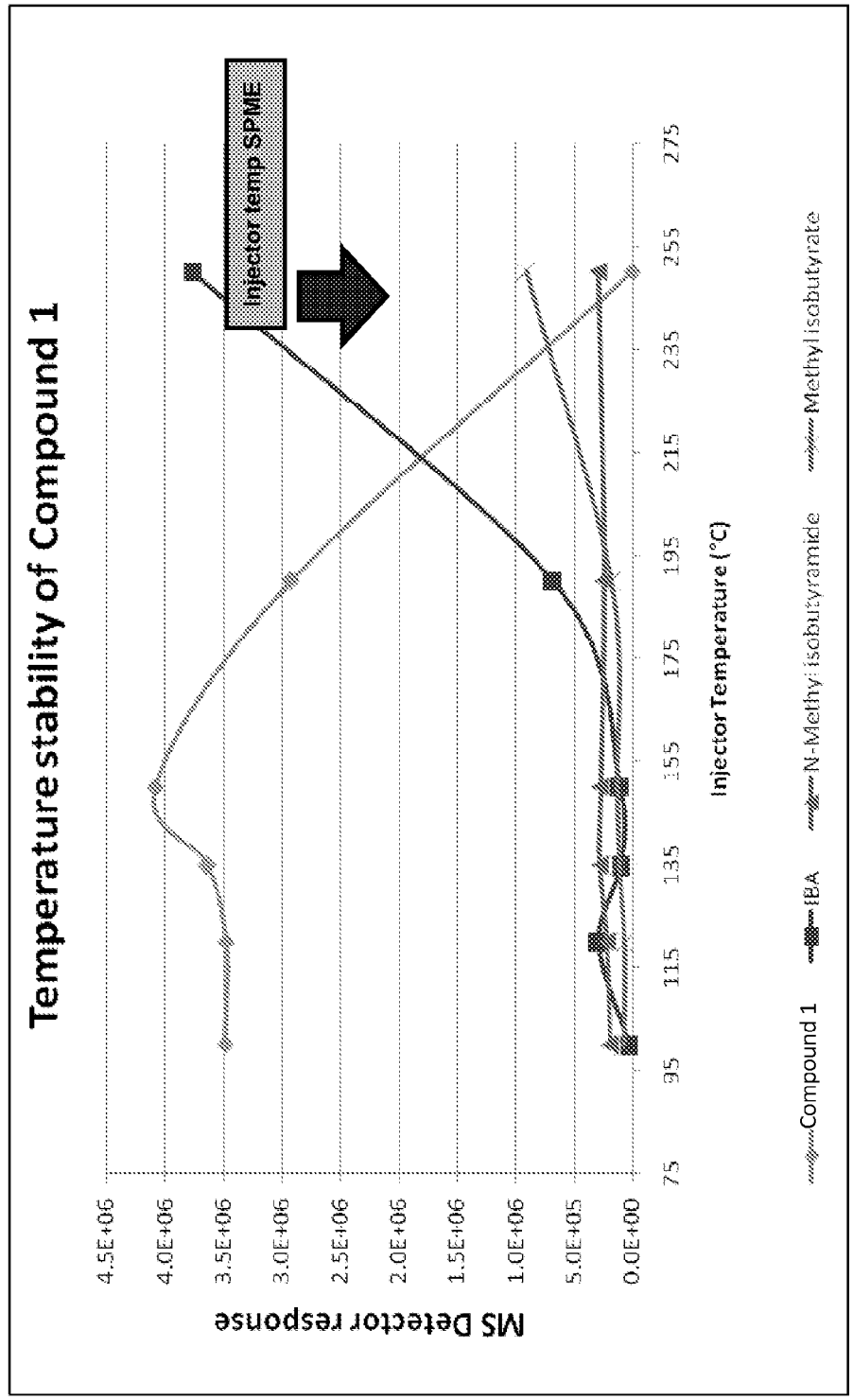
FIG. 4 demonstrates the temperature lability of N-methyl N-nitroso isobutyramide.

FIG. 4 illustrates an exemplary GC/MS profile VOCs from *M. albus* as trapped by a sorbent and eluted by ethanol as described herein. The GC/MS demonstrates peaks that have not previously been identified. The peaks at a retention time of 14.12 min and 8.55 min have been found, as described herein, to correspond to N-methyl isobutyramide and N-methyl N-nitroso isobutyramide, respectively.

Figure 5:
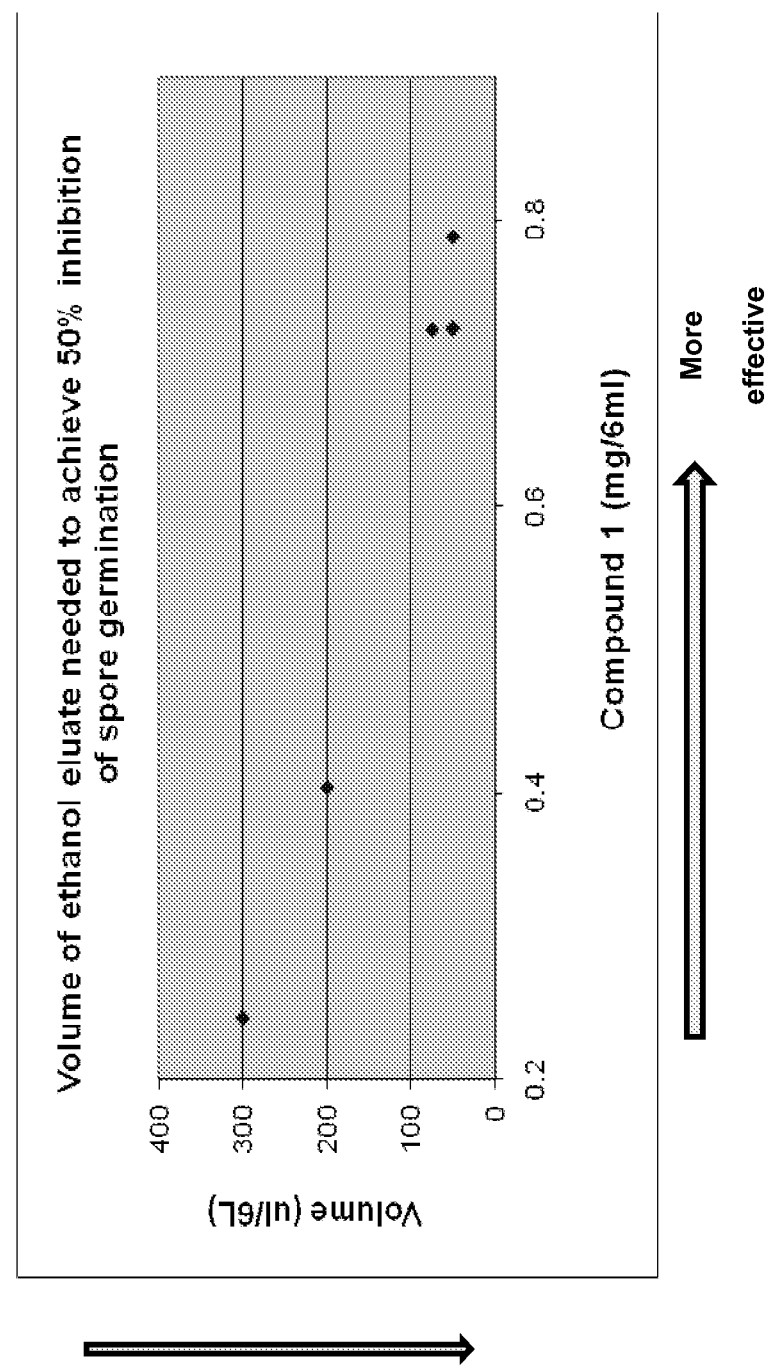
FIG. 5 illustrates the bioactivity of N-methyl N-nitroso isobutyramide and ethanol eluate as obtained by the methods provided herein to achieve 50% inhibition of spore germination.

FIG. 5 demonstrates the temperature lability of N-methyl N-nitroso isobutyramide. As shown at a standard GC/MS injection temperature of 250° C., N-methyl N-nitroso isobutyramide is not detected as it most likely has broken down into other compounds. Therefore, this compound has never been previously identified. However, as demonstrated in FIG. 5, when the injection temperature is less than 175° C., significant amounts of N-methyl N-nitroso isobutyramide are present.

Figure 6:
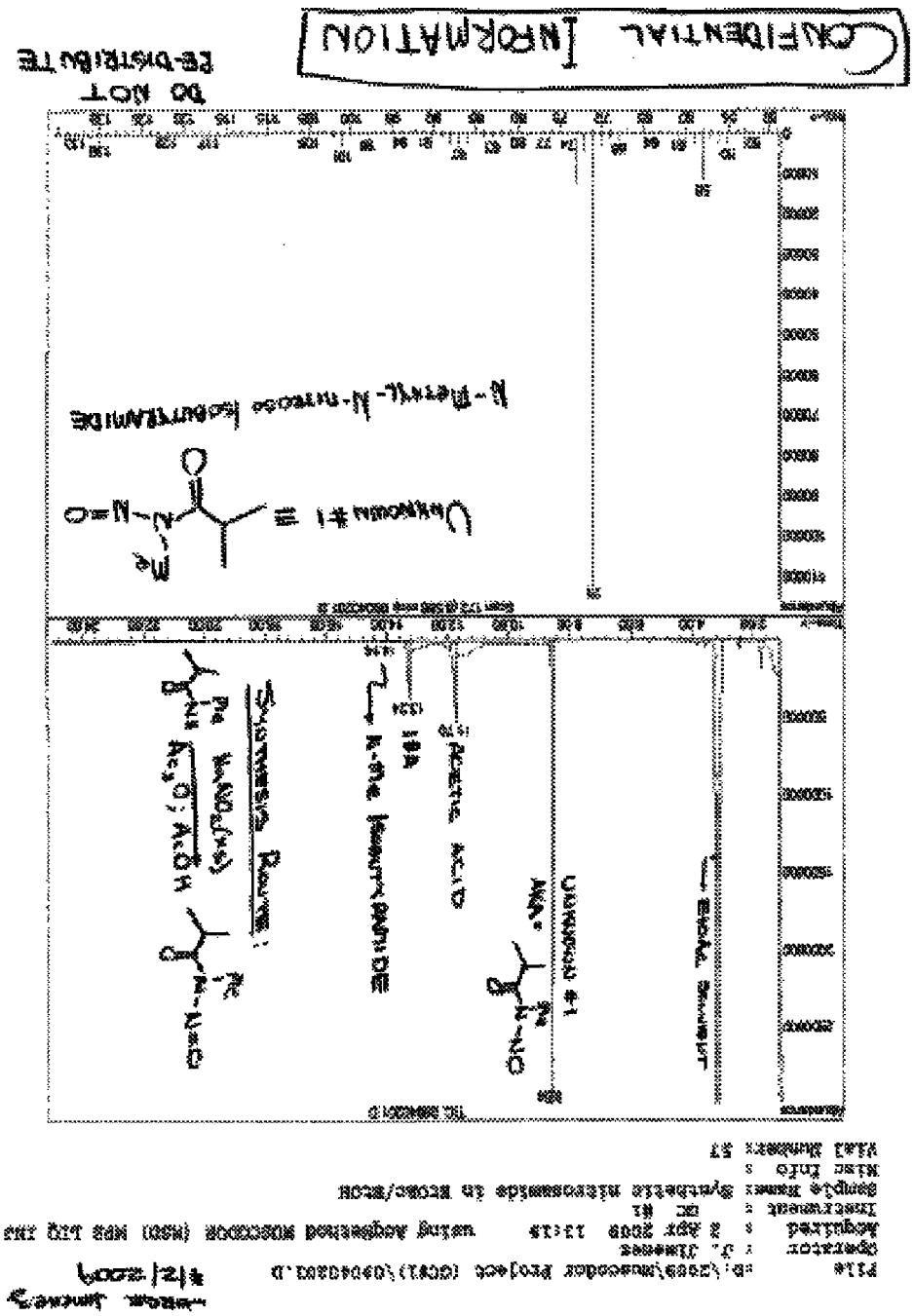
FIG. 6 illustrates a GC/MS analysis of the VOCs from *M. albus* as obtained and analyzed by the methods described herein.

FIG. 6 illustrates the bioactivity of synthetic N-methyl N-nitroso isobutyramide and an ethanol solution containing N-methyl N-nitroso isobutyramide obtained by the methods of collection and desorption from sorbents provided herein to achieve 50% inhibition of spore germination of *Penicillium expansum*. As the amount of N-methyl N-nitroso isobutyramide increases in the volume of the ethanol eluate, the ethanol eluate becomes significantly more effective at inhibiting spore generation.

Figure 7:
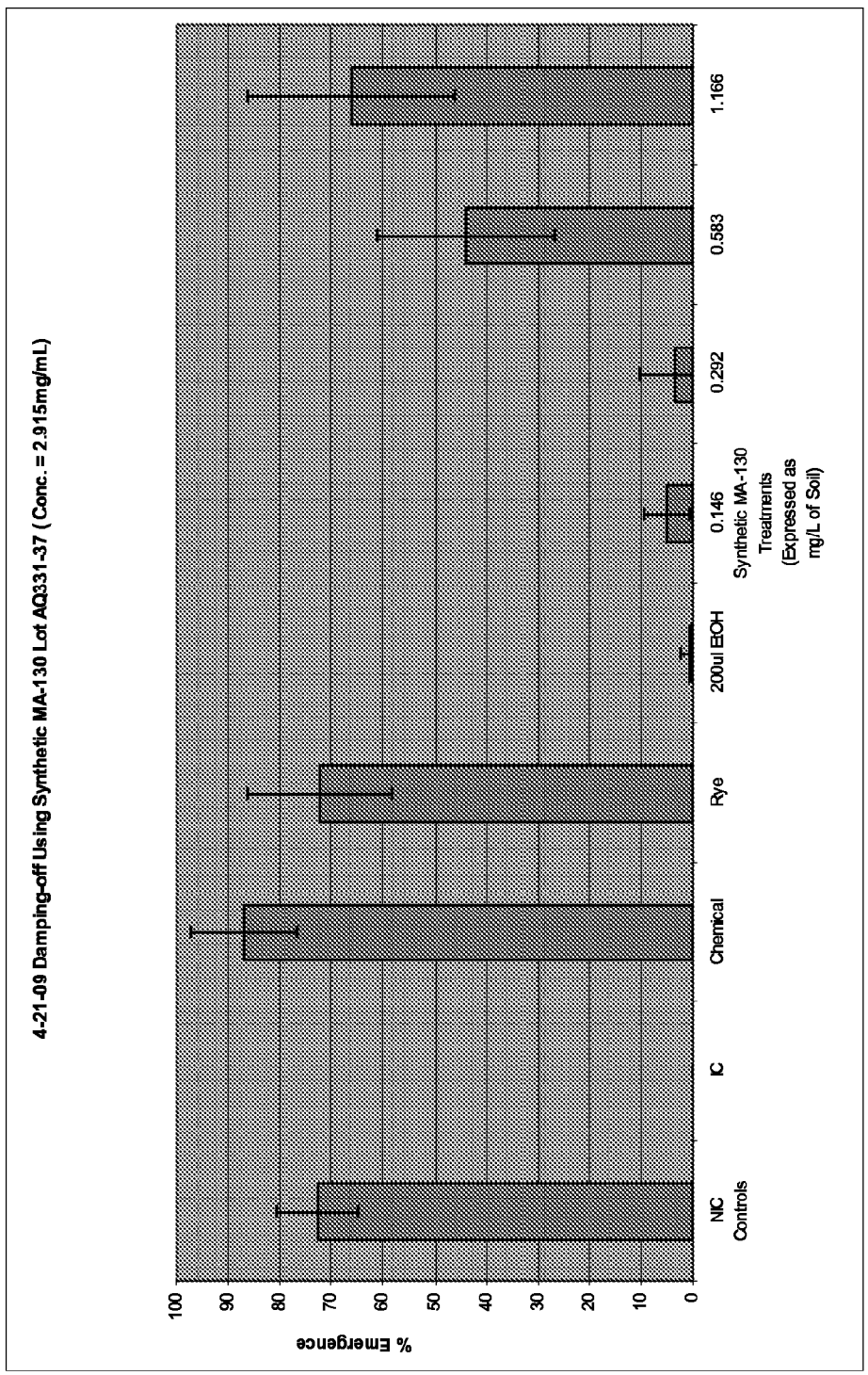
FIGS. 7 and 8 illustrate the control of damping off (*Rhizoctonia solani*) in soil and potting mix.

FIG. 7 illustrates a GC/MS analysis of the VOCs from *M. albus* as obtained and analyzed by the methods described herein. Also described is a sample formulation route for the VOCs.

Certain Chemical Terminology

Unless defined otherwise, all technical and scientific terms used herein have the same meaning as is commonly understood by one of skill in the art to which the claimed subject matter belongs.

It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting.

Definition of standard chemistry terms is found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques are used for chemical syntheses, chemical analyses, pharmaceutical preparation, formulation, and delivery, and treatment of patients. Reactions and purification techniques are performed e.g., using kits of manufacturer's specifications or as commonly accomplished in the art or as described herein. The foregoing techniques and procedures are generally performed of conventional methods well known in the art and as described in various general and more specific references that are cited and discussed throughout the present specification. Throughout the specification, groups and substituents thereof are chosen by one skilled in the field to provide stable moieties and compounds.

Unless otherwise noted, the use of general chemical terms, such as though not limited to "alkyl," "amine," "aryl," are equivalent to their optionally substituted forms. For example, "alkyl," as used herein, includes optionally substituted alkyl.

In some embodiments, the compounds presented herein possess one or more stereocenters. In some embodiments, each center exists in the R or S configuration, or combinations thereof. Likewise, in some embodiments, the compounds presented herein possess one or more double bonds. In some embodiments, each exists in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. For techniques regarding inverting or leaving unchanged a particular stereocenter, and those for resolving mixtures of stereoisomers see, for example, Furniss et al. (eds.), VOGEL'S TEXTBOOK OF PRACTICAL ORGANIC CHEMISTRY 5$^{th}$ Edition, Longman Scientific and Technical Ltd., Essex, 1991, 809-816.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined below. Further, in some embodiments, an optionally substituted group is unsubstituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible.

As used herein, C$_1$-C$_x$ includes C$_1$-C$_2$, C$_1$-C$_3$ ... C$_1$-C$_x$. By way of example only, a group designated as "C$_1$-C$_4$" indicates that there are one to four carbon atoms in the moiety, i.e. groups containing 1 carbon atom, 2 carbon atoms, 3 carbon atoms or 4 carbon atoms, as well as the ranges C$_1$-C$_2$ and C$_1$-C$_3$. Thus, by way of example only, "C$_1$-C$_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl. Whenever it appears herein, a numerical range such as "1 to 10" refers to each integer in the given range; e.g., "1 to 10 carbon atoms" means that the group has 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The terms "heteroatom" or "hetero" as used herein, alone or in combination, refer to an atom other than carbon or hydrogen. In some embodiments, heteroatoms are independently selected from among oxygen, nitrogen, sulfur, phosphorous, silicon, selenium and tin but are not limited to these atoms. In embodiments in which two or more heteroatoms are present, the two or more heteroatoms are the same as each another, or some or all of the two or more heteroatoms are each different from the others.

The term "alkyl" as used herein, alone or in combination, refers to an optionally substituted straight-chain, optionally substituted cyclic, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "C$_1$-C$_6$ alkyl" or "C$_{1-6}$ alkyl", means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The term "alkenyl" as used herein, alone or in combination, refers to an optionally substituted straight-chain, or optionally substituted branched-chain hydrocarbon monoradical having one or more carbon-carbon double-bonds and having from two to about ten carbon atoms, more preferably two to about six carbon atoms. The group is in either the cis or trans conformation about the double bond(s), and should be understood to include both isomers. Examples include, but are not limited to ethenyl (—CH═CH$_2$), 1-propenyl (—CH$_2$CH═CH$_2$), isopropenyl [—C(CH$_3$)═CH$_2$], butenyl, 1,3-butadienyl and the like. Whenever it appears herein, a numerical range such as "C$_2$-C$_6$ alkenyl" or "C$_{2-6}$ alkenyl", means that the alkenyl group consists of 2 carbon atoms, 3 carbon atoms, 4 carbon atoms, 5 carbon atoms or 6 carbon atoms, although the present definition also covers the occurrence of the term "alkenyl" where no numerical range is designated.

The term "alkynyl" refers to a type of alkyl group in which the first two atoms of the alkyl group form a triple bond. That is, an alkynyl group begins with the atoms —C≡C—R, wherein R refers to the remaining portions of the alkynyl group, which may be the same or different. Non-limiting examples of an alkynyl group include —C≡CH, —C≡CCH$_3$ and —C≡CCH$_2$CH$_3$. In one aspect, an alkynyl is a C$_2$-C$_6$ alkynyl.

The terms "heteroalkyl", "heteroalkenyl" and "heteroalkynyl" as used herein, alone or in combination, refer to optionally substituted alkyl, alkenyl and alkynyl structures respectively, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, silicon, phosphorous, tin or combinations thereof), or heteroatomic group such as though not limited to —O—O—, —S—S—, —O—S—, —S—O—, =N—N=, —N=N—, —N=N—NH—, —P(O)$_2$—, —O—P(O)$_2$—, —P(O)$_2$—O—, —S(O)—, —S(O)$_2$—, —SnH$_2$— and the like.

The terms "haloalkyl", "haloalkenyl" and "haloalkynyl" as used herein, alone or in combination, refer to optionally substituted alkyl, alkenyl and alkynyl groups respectively, as defined above, in which one or more hydrogen atoms is replaced by fluorine, chlorine, bromine or iodine atoms, or combinations thereof. In some embodiments two or more hydrogen atoms are replaced with halogen atoms that are the same as each another (e.g. difluoromethyl); in other embodiments two or more hydrogen atoms are replaced with halogen atoms that are not all the same as each other (e.g. 1-chloro-1-fluoro-1-iodoethyl). Non-limiting examples of haloalkyl groups are fluoromethyl and bromoethyl. A non-limiting example of a haloalkenyl group is bromoethenyl. A non-limiting example of a haloalkynyl group is chloroethynyl.

The term "cycloalkyl" as used herein, alone or in combination, refers to an optionally substituted, saturated, hydrocarbon monoradical ring, containing from three to about fifteen ring carbon atoms or from three to about ten ring carbon atoms. In some embodiments, the term includes additional, non-ring carbon atoms as substituents (e.g. methylcyclopropyl). Whenever it appears herein, a numerical range such as "C$_3$-C$_6$ cycloalkyl" or "C$_{3-6}$ cycloalkyl", means that the cycloalkyl group consists of 3 carbon atoms, 4 carbon atoms, 5 carbon atoms or 6 carbon atoms, i.e., is cyclopropyl, cyclobutyl, cyclopentyl or cycloheptyl, although the present definition also covers the occurrence of the term "cycloalkyl" where no numerical range is designated. The term includes fused, non-fused, bridged and spiro radicals. A fused cycloalkyl contains from two to four fused rings where the ring of attachment is a cycloalkyl ring, and the other individual rings are alicyclic, heterocyclic, aromatic, heteroaromatic or any combination thereof. Examples include, but are not limited to cyclopropyl, cyclopentyl, cyclohexyl, decalinyl, and bicyclo[2.2.1]heptyl and adamantyl ring systems. Illustrative examples include, but are not limited to the following moieties:

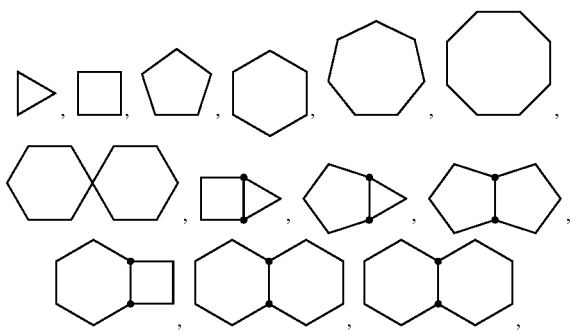

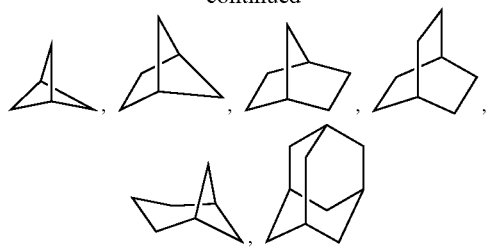

and the like.

The term "cycloalkenyl" as used herein, alone or in combination, refers to an optionally substituted hydrocarbon non-aromatic, monoradical ring, having one or more carbon-carbon double-bonds and from three to about twenty ring carbon atoms, three to about twelve ring carbon atoms, or from three to about ten ring carbon atoms. The term includes fused, non-fused, bridged and spiro radicals. In some embodiments, a fused cycloalkenyl contains from two to four fused rings where the ring of attachment is a cycloalkenyl ring, and the other individual rings are alicyclic, heterocyclic, aromatic, heteroaromatic or any combination thereof. In some embodiments, fused ring systems are fused across a bond that is a carbon-carbon single bond or a carbon-carbon double bond. Examples of cycloalkenyls include, but are not limited to cyclohexenyl, cyclopentadienyl and bicyclo[2.2.1]hept-2-ene ring systems. Illustrative examples include, but are not limited to the following moieties:

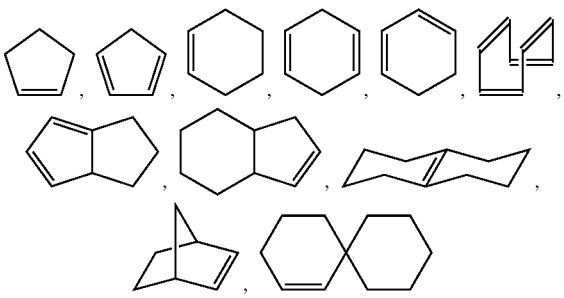

and the like.

The term "heterocyclyl" as used herein, alone or in combination, refers collectively to heteroalicyclyl and heteroaryl groups. Herein, whenever the number of carbon atoms in a heterocycle is indicated (e.g., C$_1$-C$_6$ heterocycle), at least one non-carbon atom (the heteroatom) must be present in the ring. Designations such as "C$_1$-C$_6$ heterocycle" refer only to the number of carbon atoms in the ring and do not refer to the total number of atoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). For heterocycles having two or more heteroatoms, those two or more heteroatoms are the same or different from one another. In some embodiments, heterocycles are optionally substituted. Non-aromatic heterocyclic groups include groups having only three atoms in the ring, while aromatic heterocyclic groups must have at least five atoms in the ring. In some embodiments, bonding (i.e. attachment to a parent molecule or further substitution) to a heterocycle is via a heteroatom or a carbon atom.

The terms "halogen", "halo" or "halide" as used herein, alone or in combination refer to fluoro, chloro, bromo and iodo.

The term "hydroxy" as used herein, alone or in combination, refers to the moiety —OH.

The terms "carboxy" or "carboxyl" as used herein, alone or in combination, refer to the moiety —C(O)OH, which are written as —COOH.

The term "alkoxy" as used herein, alone or in combination, refers to an alkyl ether moiety, —O-alkyl, including the groups —O-aliphatic and —O-carbocyclyl, wherein the alkyl, aliphatic and carbocyclyl groups is optionally substituted, and wherein the terms alkyl, aliphatic and carbocyclyl are as defined herein. Non-limiting examples of alkoxy radicals include methoxy, ethoxy, n-propoxy, isopropoxy, n-butoxy, iso-butoxy, sec-butoxy, tert-butoxy and the like.

It is to be understood that in instances where two or more moieties are used in succession to define a substituent attached to a structure, the first named radical is considered to be terminal and the last named radical is considered to be attached to the structure in question. Thus, for example, the radical arylalkyl is attached to the structure in question by the alkyl group.

Compounds

Novel compounds described herein comprise the structure of: Formula 2:

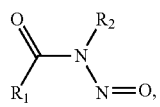

Formula 2 wherein $R_1$ and $R_2$ are each independently hydrogen or an alkyl, haloalkyl, heteroalkyl, heterocycloalkyl, halocycloalkyl, cycloalkyl, heteroalkynyl, haloalkynyl, alkynyl, haloalkenyl, heteroalkenyl or alkenyl group; or of Formula 4:

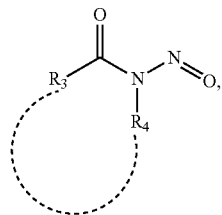

Formula 4 wherein $R_3$ and $R_4$ are attached to form a 4-, 5- or 6-membered substituted or unsubstituted heteroaryl or heterocycloalkyl group. In some embodiments, the compound is volatile under ambient conditions (for example, typical temperature and pressure for the outdoor environment). The activity of this molecule can be extended to control bacterial pathogens found in foodstuff, the prevention of mold that colonized building materials, and seed sanitation before planting to prevent fungal decay and colonization. In one aspect, a composition herein that has been discovered from *Muscodor albus* is N-methyl N-nitroso isobutyramide. The compound has been discovered to be an active substantially responsible for biological activity in *Muscodor albus* against plant and soil pathogens. Compositions herein also include analogs of N-methyl N-nitroso isobutyramide that may have similar efficacy. The analogs can be simple analogs that extend the carbon chain and branched positional isomers of such chain extensions. Volatility may be lost as the carbon chain increases, however that may not affect efficacy.

Tables 1A and 1B show several additional compounds of the invention:

TABLE 1A

Formula 2

| R1 | R2 |
|---|---|
| —$C_1$—$C_6$-alkyl | —$CH_3$ |
| —$C_2$—$C_6$-alkenyl | —$CH_3$ |
| —$C_2$—$C_6$-alkynyl | —$CH_3$ |
| —$C_1$—$C_6$-heteroalkyl | $CH_3$ |
| —$C_1$—$C_6$-alkoxy | $CH_3$ |
| —O—$C_1$—$C_6$-alkyl | $CH_3$ |
| —$C_1$—$C_3$-alkyl-O—$C_1$—$C_2$ alkyl | —$CH_3$ |
| —$C_1$—$C_4$-cycloalkyl | —$CH_3$ |
| —$CH_2$—$C_3$—$C_6$-cycloalkyl | $CH_3$ |
| —$C_1$—$C_6$-haloalkyl | $CH_3$ |

TABLE 1B

TABLE 1B-continued

[Structure: piperidinone with N-nitroso group, substituents $R_5$, $R_6$, $R_6$]

| R5 | R6 |
|---|---|
| —H | —H |
| —H | —$C_1$—$C_6$-alkyl |
| —$C_1$—$C_6$-alkyl | —H |

As described herein, methods are provided for characterizing and identifying a composition comprising a single molecule (N-methyl N-nitroso isobutyramide) or synthetic mixture or blend comprising N-methyl N-nitroso isobutyramide. In some instances, the composition comprises molecules of similar structure to N-methyl N-nitroso isobutyramide. In many instances, the compositions herein have similar biological activity to *Muscodor albus* against fungi and bacteria.

Previous work has developed a microbial rye grain formulation of *Muscodor albus* as well as a synthetic mixture was developed using commercially available chemical constituents identified from the headspace of actively growing *Muscodor albus* on rye grain. As noted above, the levels of biological activity of this synthetic mixture were inferior to those of the microbial formulation since much higher concentration levels were needed to obtain a comparable biological effect. Other strains and species of *Muscodor* produce the composition as well.

FIG. 1 illustrates products that developed from *Muscodor albus*. For example, a biological product can include a microbial formulation from *M. albus* grown on rye grain. By analyzing the VOCs in the headspace of the vessel in which *M. albus* grows, the chemical composition of the VOCs can be determined. The VOCs in FIG. 1 can be captured from the bioreactor to generate a chemical product as described herein. Exemplary capturing methods include capturing the VOCs as a sorbent as described herein. A synthetic product can also be created by creating a chemical mixture with all or some of the VOCs identified from *M. albus*. The reconstituted VOC may be used as a biocide as described herein. A synthetic composition or kit as described herein can comprise a compound of Formula 2, such as N-methyl N-nitroso isobutyramide.

Compounds of the invention may be synthesized by any known method, or as described below. For example, the following general procedure may be used to synthesize the compounds of the invention.

[Reaction scheme: Formula 1 ($R_1$C(O)NH$R_2$) → Procedure A → Formula 2 ($R_1$C(O)N($R_2$)N=O)]

Formula 1        Formula 2

In Procedure A, $R_1$ and $R_2$ are each independently hydrogen or an alkyl, haloalkyl, cycloalkyl, or alkenyl group. An exemplary procedure for synthesis of nitrosamine compounds of the invention is described in Example 3. Variations and alternative methods may be used, for example as described by White, JACS 77, 6008 (1955).

In one embodiment, R2 is a methyl group. In another embodiment in which volatility of the compounds is especially important, such as in treatment of materials in an enclosed space or container as described herein and known in the art, including treatment of post harvest pathogens in warehouses, processing plants, grain silos or trucks, treatment of tarped soils, or treatment of buildings or of medical or veterinary tools in a closed container, R1 may be a C1-C4 alkyl group (including a haloalkyl, heteroalkyl or cycloalkyl group) or a C2 alkenyl group, and R2 may be a methyl group. In still other embodiments in which volatility is not critical or not desired, R1 may be a C1-C8 alkyl group (including a haloalkyl, heteroalkyl or cycloalkyl group).

In various embodiments, the compound has a solubility in water which is about 5, about 6, about 7, about 8, about 9, about 10, about 11, about 12 or about 13 g/L. In one embodiment, the compound has a solubility in water which is from about 5 to about 13 g/L. The solubility can be measured as specified by the applicable US EPA Office of Prevention, Pesticides and Toxic Substances standard. For example, the solubility of the compound is about 8 g/L.

In other various embodiments, the compound has a vapor pressure which is about 5, about 10, about 15, or about 20 torr. In one embodiment, the compound has a vapor pressure that is from about 5 torr to about 20 torr. In another embodiment, the compound has a vapor pressure that is from about 10 torr to about 15 torr. The vapor pressure can be measured as specified by the applicable US EPA Office of Prevention, Pesticides and Toxic Substances standard. For example, the vapor pressure of the compound is about 15 torr.

Without wishing to be bound by any particular theory, Applicant hypothesizes that the compounds of the present invention derive some of their unique fumigant and curative properties because they are both water soluble and volatile, which is a somewhat unique combination. Therefore, in still other embodiments, the compound has a solubility in water which is about 5, about 6, about 7, about 8, about 9, about 10, about 11, about 12 or about 13 g/L and a vapor pressure that is about 5, about 10, about 15 or about 20 torr. In one embodiment, the compound has a water solubility of from about 5 to about 13 g/L and a vapor pressure of from about 10 torr to about 15 torr. In one particular embodiment the solubility is about 9 g/L and the vapor pressure is about 15 torr.

Applications

The compound of the present invention is useful for various applications related to control of microorganisms, such as bacteria and fungi, or pests, such as insects, mites and nematodes, either alone or combined with a carrier or delivery agent in a kit or compositions, as described below. The carrier, delivery agent or delivery device selected will depend upon the desired application.

In general, an effective amount of the compounds of the present invention is applied to a target pathogen or pest or to a locus where control of such target pathogen or pest is desired. In one embodiment, the compound is applied to materials on which control of a target pathogen or pest is desired. Application to a material refers to application to soil; seed; food, whether processed, minimally processed, or simply harvested and unprocessed; finished and unfinished goods, such as medical and veterinary devices and tools, including endoscopes; buildings, including storage facilities and greenhouses; and other types of enclosed containers, including ship hulls, grain silos and boxes of fruits and vegetables. It excludes application to humans or animals for therapeutic purposes.

The compounds of the present invention may be used in pre-harvest agricultural applications; for food safety applications; to sanitize medical and veterinary equipment, including to eliminate biofilms; and for the treatment of construction materials and buildings and finished goods such as clothing, books and artwork. For example but without limitation, methods are provided herein for using the compounds, compositions and/or kits described herein for soil treatment for the control of soil-borne pathogens and control of invertebrate pests, including nematodes; post-harvest fumigation of foodstuff, including in storage facilities or in bins during shipment to prevent fungal decay and bacterial contamination; fumigation of stored grains for the control of insects; fumigation of building material to prevent mold colonization after water intrusion; and fumigation and sanitation of meat and meat-products; and preservation of packaged, minimally processed foods, such as spinach and lettuce and of processed food that is susceptible to fungal infection, such as bread. Post harvest refers to fruit, vegetables and nuts after harvest from the field but before packaging.

In pre-harvest agricultural applications, the compounds of the present invention are used in methods for treating or protecting fruit, seeds, plants or the soil surrounding the plants from an infestation by an organism selected from the group consisting of a fungus, a bacteria, a microorganism, an insect, and other invertebrate pests by applying to the organism or to a locus inhabited by the organism an effective amount of the composition. The term control, as used herein, refers to killing or inhibiting the growth of microorganisms or to killing insects, nematodes and/or mites; inhibiting the activity of insects, nematodes and/or mites (e.g., reduced mobility, appetite and/or reproductive capability); or repelling insects and/or mites from a host or area. In pre-harvest agricultural applications, an effective amount of a compound is an amount effective to control microorganisms or insects, nematodes or mites and/or to reduce plant or seed damage and/or increase plant growth.

For example, a method herein can comprise delivering a compound to soil. Before sowing seeds in plowed earth, it is desirable to destroy unwanted and harmful forms of life, such as soil borne pathogens, worms, insects and certain vegetable life forms, which may destroy the seeds or interfere with their proper germination. In an embodiment, the application of a composition herein penetrates into the soil. In some instances, steam is used to destroy soil-borne pathogens. In an embodiment a method of delivering a composition to soil herein comprises delivering the composition with steam. In an embodiment, a composition herein is delivered with solar radiation. For example, a method herein can comprise spreading plastic sheets over soil.

Exemplary soil borne pathogens include, but are not limited to: *Aphanomyces cochlioides, Fusarium avenaceum, Fusarium culmorum, Phytophthora capsici, Phytophthora cinnamomi, Pythium ultimum, Rhizoctonia solani, Sclerotinia sclerotiorum, Sclerotinia minor, Sclerotium rolfsii, Ustilago hordei, Stagonospora nodorum, Aspergillus fumigatus, Verticillium dahliae, Tapesia yaliunde, Alternaria alternate* and *Penicillium expansum*. In one embodiment, the compounds are soil fumigants that may be used as an alternative to methyl bromide for controlling soil-borne pathogens.

In some instances, methods are disclosed wherein the compounds herein are used to inhibit the growth of or kill an organism that is a nematode (or soil-borne pest). Exemplary soil borne pests include, but are not limited to: *Meloidogyne incognita, Meloidogyne chitwoodi, Meloidogyne hapla, Paratrichodorus allius, Pratylenchus penetrans*, and *Caenorhabditis elegans*.

In various embodiments wherein the treatment is for the protection of soil, the compound of Formula 2 or Formula 4, or prodrug thereof, is provided in an amount of about 0.5 mg/L of soil/potting mix to about 200 mg/L of soil/potting mix. In some of the specific embodiments, the compound is present in an amount of about 0.5 mg/L soil to about 2.0 mg/L soil, or from about 0.5 mg/L soil to about 5.0 mg/L soil, or from about 0.5 mg/L soil to about 10.0 mg/L soil, or from about 0.5 mg/L soil to about 20.0 mg/L soil, or from about 0.5 mg/L soil to about 30.0 mg/L soil, or from about 0.5 mg/L soil to about 40.0 mg/L soil or from about 0.5 mg/L soil to about 50.0 mg/L soil, or from about 0.5 mg/L soil to about 70.0 mg/L soil. Depending on the environment, one of skill in the art will be able to optimize the amount of the compound of Formula 2 or Formula 4 per Liter of soil to achieve the maximum success.

Compounds of the invention may be used in agricultural applications using any known delivery method, or as provided herein. For example, compounds of the invention may be applied to soil through methods including, but not limited to, shank injection, sprays, granules, flood/furrow methods, sprinklers, and drip irrigation.

In one embodiment, shank injection is used to deliver compounds of the invention to soil. Traditional fumigation may be used, where the compound is injected below the surface of the soil and applied in a narrow band as the fumigation equipment is moved across the field. Subsequently, the surface of the soil is sealed or compacted using a ring roller attached behind the fumigation equipment or behind a second tractor. Different depths of injection and shank spacings may be used as appropriate. Generally, deeper injections and closer shank spacings provide increased control in well prepared soils but require larger and more costly equipment to perform.

In another embodiment, a spray is used to deliver the compound of the invention to soil. The compound may be dissolved in the liquid to be applied or may be delivered as an emulsion or microemulsion. Both preplant and postplant application can be used. Following application, any number of incorporation methods may be employed, such as irrigation or mechanical incorporation. Various depths of incorporation can be achieved depending on the method of incorporation used (1-2 inches for a Lilliston, 3-4 inches using a rotera and 6-8 inches with a rototiller). A cover may be used to aid incorporation, such as a polyethylene mulch layer or a tarp.

In other embodiments, granules or microcapsules can be used to deliver the compounds of the invention. Granules may be delivered using a granular applicator such as a Gandy box. Following application, incorporation is generally done via irrigation or mechanical methods as described for spray methods. Covers may also be used.

In still other embodiments, flood basin or furrow irrigation may be particularly useful to deliver the compounds of the invention. In these methods, the compound is delivered mixed or dissolved in the water applied to the soil. Uniform and rapid movement of the treated water is desirable, which can be enhanced by pre-irrigation with regular water, followed by draining and application of the treatment. Barriers are typically used to contain the treated area, and pumps may be used to apply the necessary water.

In some embodiments, sprinklers are used to deliver a solution or suspension of the compound of the invention to the surface of the soil, allowing the compound to be delivered over the entire irrigation cycle.

In other embodiments, the compound of the invention is applied through drip irrigation lines (drip fumigation). For example, the compound is injected over the entire irrigation cycle. Concentrated product can be added to a differential pressure tank and diluted over a period of time during the application. Water from the drip line enters the drip irrigation device, mixes with the product and is returned to the drip line, resulting in a solution of the appropriate concentration which can subsequently be applied to the soil. Pumps may be used as necessary to aid movement of liquid. Drip irrigation tubing can be placed on the ground surface or buried beneath the surface. The present invention may also be used in portable drip applicators. Spacing and flow rate of the drip irrigators can be chosen depending on the soil type and crop, and can be adjusted to provide the desired distribution of liquid.

The kits and compounds herein can be combined with a controlled release delivery system in order to time-release the bioactive agents. Such controlled release delivery systems include methods, known in the art, of encapsulation, dissolution, or incorporation of the active ingredient.

If desired, a compound of the invention can be used in combination with other pesticides (such as other types of fumigants). For example, the compounds herein may be used together with inert gases (such as nitrogen, noble gases) and/or carbon dioxide. The inert gases and carbon dioxide can serve as auxiliary gases, for example as carrier gases in compounds with a higher boiling point. Other fumigants can also serve as carrier gases.

In addition to soil fumigation applications, the compounds of the present invention may be used for seed treatment. The concept of seed treatment is the use and application of biological and chemical agents that control or contain primary soil and seed borne infestation of insects and/or diseases which can pose devastating consequences to crop production. Typically, seed treatment involves treating seeds in order to inhibit growth of soil-borne pathogens after planting, while seed sanitation generally involves treating seeds to inhibit the growth of seed-borne diseases before planting. Diseases suitable for treatment by these approaches include, but are not limited to, loose smut of barley (*Ustilago nuda*), infections of Lettuce Mosaic Virus, *Ascochyta* leaf and pod spot of field beans (*Didymella fabae*), and Pea bacterial blight (*Pseudomonas syringae*). The compounds of the present invention may be used for controlling the growth of seed-borne pathogens such as *Ustilago hordei* and *Penicillium expansum.*

In some instances, a method of delivering a composition herein is to treat seeds. In some instances, compositions herein increase seed germination. In other instances, compositions and methods herein improve seedling emergence. In some instances, compositions and methods herein protect seeds or seedlings from early season diseases and insect pests, thereby improving the crop. Seed treatment methods herein can protect seeds from seed and soil-borne diseases and also gives protection to the emerged seedlings from insect pests affecting crop emergence and its early growth. In some instances, a delivery system for a composition herein for seed treatment comprises a dressing. A composition for a seed dressing can be wet or dry. In some instances, a method of delivering a composition to a seed is delivered at a farm or at an industry. In an embodiment, a method comprises mixing a composition herein. The seed can be spread on a polyethylene sheet and required quantity of composition can be sprinkled on seed lot and mixed mechanically by the user.

In some instances, a delivery system for a composition herein for seed treatment comprises a pellet.

In some instances, a delivery system for a composition herein for seed treatment comprises a seed coating. A delivery system can comprise a special binder used with a formulation to enhance adherence to the seed. The compounds can also be applied to seed in a suitable manner known in the art such as, for example, spraying, atomizing, vaporizing, scattering, dusting, watering, squirting, sprinkling, pouring, fumigating, and the like. They can also be used for seed treatment or sanitation as a pre-treatment for storage or sowing. For example, the seed may form part of a pelleted composition or, alternatively, may be soaked, sprayed, dusted or fumigated.

The compounds of the invention may be used to treat insects, such as aphids or thrips, and mites. In some embodiments, the compound is applied to empty greenhouses to control pests that are present before plants are transferred into the greenhouse.

In other embodiments, the compounds may be used for whole plant fumigation to control pathogens and pests, as allowed by phytotoxicity of the compound as to a particular plant. For example, powdery mildew may be treated in cucumbers using whole plant fumigation. However, the compound causes phytotoxicity in other plants. One of skill in the art will know how to test plants for phytotoxicity to determine whether whole plant fumigation is feasible.

In some instances, the compounds, compositions, kits and methods herein provide a more cost effective and more convenient way to deliver the active volatiles when compared to rye formulations of *Muscodor albus* wherein disposal of the rye grain after treatment can be a problem. They also overcome the challenges that arise with importing and exporting containers of post-harvest foods, such as fruits, vegetables and nuts to which a live microorganism has been applied.

A compound herein can be used to destroy post harvest pathogens. In some instances, a composition is delivered in a dip solution. In some instances, a composition herein can be delivered with brushes. For example, a composition is misted over saturated brushes. In some instances, a composition is sprayed on a crop post harvest to control pathogens. In some instances, a composition herein can be delivered with an oil carrier, such as a wax. In some instances, a composition herein is used for food safety applications.

Exemplary post harvest pathogens include, but are not limited to: *Botrytis cinerea* (gray mold), *Colletotrichum acutatum, Colletotrichum coccodes* (anthracnose), *Erwinia carotovora* (bacterial soft rot), *Geotrichum candidum, Geotrichum citri-aurantii* (sour rot), *Helminthosporium solani* (silver scurf of potato), *Monilinia fructicola* (brown rot), *Penicillium digitatum* (green mold of citrus), *P. expansum* (blue mold of pome fruits), *Rhizopus* sp. (Rhizopus rot or leak), and *Aspergillus niger* (black mold).

In various embodiments, the compound is used for post-harvest applications to fruit. In some of the specific embodiments, the amount of the compound per volume of air in a container holding the fruit is about 10 μg/L air to about 50 mg/L air. In some embodiments, the amount of compound per volume of air in a container holding the fruit is about 10 μg/L air to about 10 mg/L air.

In food safety and some other applications involving treatment of microorganisms, sanitizing is important. As used herein, sanitizing means controlling the growth and reproduction of microbial contaminants or pathogens to safe levels as judged by public health requirements. In one embodiment, this is a at least a 1 log reduction in cell number, in another embodiment at least a 2 log reduction, in another at least a 3 log reduction, in another at least a 4 log reduction, and in another at least a 5 log reduction.

In many instances, methods herein can be used for controlling the known storage pests and material pests, such as the tobacco beetle, the grain weevil, moths, such as flour or clothing moths, flour mites, flour beetles, rice weevils, deathwatch beetles, woodworms, house longhorn beetle, potato tuber moths, ham mites, or carpet beetles.

The compounds may also be used to control or prevent the growth of human food-borne pathogens, such as *Escherichia coli, Salmonella, Listeria, Clostridium, Staphylococcus aureus, Aspergillus,* or *Penicillium* in processed foods, such as dairy products, breads, tortillas, deli meats, and bakery products; semi-processed or minimally processed foods, such as meat and cut fruit and vegetables; and packaged foods, such as packaged lettuce, spinach and other vegetables.

In some instances, the compositions described herein are used to inhibit the growth of or to kill an organism that is an insect. Both structural and post-harvest pests may be targeted. Exemplary insects include, but are not limited to: *Blatella germanica* (cockroach, structural pest), *Cydia pomonella* (codling moth, post-harvest pest), *Plodia interpunctalla* (indian meal moth, post-harvest pest), *Tribolium castenatum* (confused flour beetle, post-harvest pest), *Frankliniella occidentalis* (w. flower thrips), *Myzus persicae* (green peach aphids), *Pseudococcus maritimus* (grape mealy bug), *Tetranicus pacificus* (pacific spider mite), *Aedes aegypti* (yellow fever mosquito), *Phthorimaea operculla* (potato tuber moth, post harvest pest), and *Spodoptera exigua* (beet armyworm).

The compounds are further useful for treating human or animal waste and for treating and/or preventing mold infestations of construction materials, such as wood and drywall, and existing structures, such as buildings and crawlspaces within buildings. The compound herein can be used to treat or prevent toxic mold on building materials and in buildings by contacting the building, the building materials, or the spaces between the building materials with the compounds. In some instances, a composition herein can be used alone or in combination with other fumigants in a room or, alternatively, during whole building fumigations.

Pathogens that contribute to building mold and that may be controlled by the compositions of this invention include *Acremonium strictum, Aspergillus niger, Aspergillus versicolor, Chaetomium globosum, Eurotium amstelodami, Paecilomyces variotii, Penicillium brevi-compactum, Penicillium chrysogenum Penicillium citrinum, Penicillium expansum, Cladosporium cladosporioides, Scopulariopsis brevicaulis, Trichoderma viride, Alternaria alternate* and *Stachybotrys,* including *Stachybotrys chartarum*. In other instances, the compounds of the invention may be used for removal of ants, termites or moths.

Compositions can also be used to treat human or animal waste or to reduce odors in such waste, for example, as a component of a waste water or solid management or treatment. They also are useful to decontaminate human and animal waste, for example, decrease or remove bacterial and fungal contamination. In various embodiments, the compound is used for building mold applications. In some of the specific embodiments, the compound is present in an amount of about 20 µg/L air to about 20 mg/L air, and optimal application rates may be determined by routine experimentation by one of ordinary skill in this field.

In some instances, methods are disclosed wherein the compositions herein are used to inhibit the growth of or kill an organism that is a human pathogen. For example, the compositions and methods of the invention are used to improve the safety of food products or in other food safety applications. Exemplary human pathogens include, but are not limited to *E. coli, Listeria, Salmonella, Enterobacter, Clostridium, Staphylococcus aureus, Aspergillus,* and *Penicillium*. In some instances, the pathogen to be treated is *Corynebacterium renale* (ATCC 10848), *Klebsiella pneumoniae, Proteus mirabilis, Enterobacter cloacae, Clostridium sporogenes, Legionella pneumophila, Streptococcus pyogenes,* Methicillin Resistant *Staphylococcus aureus* (MRSA), *E. coli* 0157: H7, *Shigella dysenteriae, Bacillus cereus,* or *Listeria monocytogenes.*

In some embodiments, the methods and compositions of the invention are used in medical or veterinary applications. For example, the compounds of the invention are used in the sanitization of medical devices and tools (such as endoscopes and instruments that penetrate the body).

In other embodiments, biofilms formed by pathogenic or undesirable organisms are removed or destroyed. Biofilms are dense aggregates of microorganisms embedded in a polysaccharide matrix and are common in moist environments. Their formation has implications not only in a medical or veterinary context, but also other areas such as water sanitation and food safety. For example, biofilms may form in drinking water or they may form in a small cut present in a piece of fruit. Because pathogenic organisms can grow within biofilms, it is often desirable to destroy such biofilms as efficiently as possible. This can be a difficult task because biofilms comprise a protective shell of bacteria that is not penetrable by many chemicals.

Other human pathogens suitable for application of compounds of the invention in medical and veterinary settings are *Staphylococcus aureus* (including MRSA), *Clostridium difficile* (including colitis-causing *C. difficile*), *Escherichia coli, Enterobacter* spp., *Acinetobacter baumannii,* Coagulase negative *staphylococci, Pseudomonas aeruginosa, Stenotrophomonas maltophilia, Enterococcus* (including Vancomycin-Resistant *Enterococcus*), and *Legionella*.

In some embodiments, the compounds of the present invention are administered as a therapeutic and provided is a pharmaceutical composition comprising a therapeutically effective amount of a composition herein, or a pharmaceutically acceptable salt thereof, and at least one pharmaceutically acceptable inactive ingredient. In one aspect, the pharmaceutical composition is formulated for intravenous injection, subcutaneous injection, oral administration, inhalation, nasal administration, topical administration, ophthalmic administration or otic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

Pharmaceutical formulations described herein are administerable to a subject in a variety of ways by multiple administration routes, including but not limited to, oral, parenteral (e.g., intravenous, subcutaneous, intramuscular), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

A pharmaceutical composition, as used herein, refers to a mixture of a composition herein with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

Other exemplary applications of the compounds and kits herein include without limitation: a pharmaceutical for wounds, for example in wound dressings; in other medical or veterinary applications; in sanitization of medical or veterinary equipment; as a biocide, for example for control of algae, protozoa; as a fumigant in grain elevators, mills, ships, clothing, furniture and greenhouses.

The examples herein demonstrate that some of the efficacy of *Muscodor albus* (for example the rye grain formulation) is attributable to the compositions described herein such as N-methyl N-nitroso isobutyramide. For example, activity against *P. expansum* of a synthetic mixture not comprising N-methyl N-nitroso isobutyramide was compared to a synthetic mixture comprising N-methyl N-nitroso isobutyramide. Only the composition comprising N-methyl N-nitroso isobutyramide demonstrated significant activity. When the composition comprising N-methyl N-nitroso isobutyramide was heated and then tested for efficacy, it was shown to have decreased efficacy, as N-methyl N-nitroso isobutyramide appears to be heat unstable. Also provided in the examples herein, synthetically produced N-methyl N-nitroso isobutyramide has shown potent biocidal activity alone against *P. expansum* in in vitro studies and *Rhizoctonia solani* in soil studies.

Fumigation using the compounds of the present invention may be useful in several applications. It may be carried out in several steps and the delivery amount or concentration can be altered between steps. As an alternative, fumigation may also be carried out using fumigants that are known ovicides, for example, in combination with hydrocyanic acid, formic acid esters, alkylisothiocyanates or $PH_3$.

For example, rooms where the pathogens and/or pests reside can be fumigated, such as storage areas, museums, churches, mills, cargo holds of ships, railroad cars, and silos. Individual goods to be fumigated can be placed into mobile tents. Mobile chambers, containers, and buildings can be fumigated. In many instances, the application of the compounds, compositions, and kits herein in done in a closed environment. In some embodiments, the compound of Formula 2 or Formula 4 is provided in an amount of about 0.1 mg/L air to about 100 mg/L air. Depending on the closed environment, one of skill in the art will be able to optimize the amount of the compound of Formula 2 or Formula 4 per Liter of air to achieve the maximum success. For example, it can be useful to seal the corresponding rooms or containers, so that no fumigant can reach the environment. The containers or buildings can also be wrapped in foil in a known manner to prevent treatment gas from escaping into the atmosphere. A seal to prevent gas exchange can also be ensured by adhesive tape, strippable coatings, or caulking. Both installed or uninstalled building timber can be treated. For instance, freshly cut or sawed timber can be placed into a tent, a fumigation chamber, or a foil envelope for fumigation. This can prevent the spreading of pests in export/import applications (quarantine fumigation).

The formulation can also be prepared for application as a fumigant for both outdoor as well as indoor application, for example in closed environments, such as greenhouses, animal barns or sheds, human domiciles, and other buildings. Various methods for preparing fumigants can be used, for example, as fogging concentrates and smoke generators. A fogging concentrate is generally a liquid formulation for application through a fogging machine to create a fine mist that can be distributed throughout a closed and/or open environment. Such fogging concentrates can be prepared using known techniques to enable application through a fogging machine. Fumigations in a closed environment may be followed by a venting step before the closed environment is opened or approached.

In various embodiments, the compound has between about 75% and about 100% growth inhibition of fungi and bacteria over a 24 hour period when the compound is present in an amount of between about 2 µg/L air to about 50 µg/L air. In some embodiments, the compound has between about 90% and about 100% growth inhibition. In some embodiments, the compound has a growth inhibition of fungi of about 80%, or about 90% or 100%. In some specific embodiments, the compound is present in an amount of about 5 µg/L air, or about 10 µg/L air, or about 20 µg/L air, or about 30 µg/L air, or about 40 µg/L air, or about 50 µg/L air. In some embodiments, the concentration of the compound is between about 0.5 mg/ml to about 2.5 mg/ml. In some embodiments, the concentration is about 1 mg/ml.

In various embodiments, the compound has between about 75% and about 100% growth inhibition of fungi and bacteria over a 48 hour period when the compound is present in an amount of between about 2 µg/L air to about 50 µg/L air. In some embodiments, the compound has between about 90% and about 100% growth inhibition. In some embodiments, the compound has a growth inhibition of fungi of about 80%, or about 90% or 100%. In some specific embodiments, the compound is present in an amount of about 5 µg/L air, or about 10 µg/L air, or about 20 µg/L air, or about 30 µg/L air, or about 40 µg/L air, or about 50 µg/L air. In some embodiments, the concentration of the compound is between about 0.5 mg/ml to about 2.5 mg/ml. In some embodiments, the concentration is about 1 mg/ml.

In various embodiments, the compound has between about 75% and about 100% growth inhibition of fungi and bacteria over a 24 hour period when the compound is present in soil in an amount of between about 0.5 mg/L to about 70 mg/L. In some embodiments, the compound has between about 90% and about 100% growth inhibition. In some embodiments, the compound has a growth inhibition of fungi of about 80%, or about 90% or 100%.

In various embodiments, the compound has between about 75% and about 100% growth inhibition of fungi and bacteria over a 48 hour period when the compound is present in soil in an amount of between about 0.5 mg/L to about 70 mg/L. In some embodiments, the compound has between about 90% and about 100% growth inhibition. In some embodiments, the compound has a growth inhibition of fungi of about 80%, or about 90% or about 100%.

In many instances, a composition can be used as an alternative or as a substitute or in combination to natural gaseous byproducts produced by *Muscodor fungi*.

Gases produced by *Muscodor* and the compositions herein are useful to inhibit the growth of or kill an organism selected from the group consisting of a fungus, a bacteria, a microorganism, a nematode, an insect and other invertebrate pests. In some instances, methods known to those of skill in the art can be used to contact an organism in an amount effective to kill or inhibit the growth of the organism. In one embodiment the organisms are phytopathogenic.

Kits and Compositions Comprising Delivery Agents or Devices

The compounds of the present invention may be formulated with a carrier or delivery agent or provided with a delivery device or delivery agent that is suitable for the desired application.

Provided herein are kits or compositions comprising a pesticide that comprises a compound of Formula 2 or Formula 4 and a delivery agent that comprises a pesticide-acceptable solvent, carrier, co-formulant or diluent. In some instances, the compositions herein comprise a compound of the present invention and a suitable delivery agent or carrier. In other instances, a kit herein can comprise a compound herein and a delivery agent.

In some embodiments, the delivery agent is a liquid, which may be a solution of the compound with a compatible solvent/diluents or a stabilized mixture such as an emulsion or microencapsulated formulation. In some embodiments, the liquid is one from which or with which the compound volatilizes under ambient conditions (for example, typical temperature and pressure for the outdoor environment). In some liquid embodiments, the delivery agent may include a propellant, a volatile liquid, or a dip or coating for an object. In such dip or coating embodiment the object can be a fruit, vegetable or other food item. In other embodiments, the delivery agent is liquid based fogging agent.

In other embodiments, the delivery agent may be a solid. In some embodiments, the solid is a gel containing the compound. In still other embodiments, the delivery agent is a solid, such as a solid matrix. In some embodiments the solid matrix is film or tape. In other solid embodiments, the compound may be incorporated into a tape, film or package. Such an embodiment could be released upon a specific treatment such as wetting. In another embodiment, the compound could be incorporated into a dressing for a wound. An alternative solid embodiment would include a granule containing the compound.

In another embodiment, the compound can be incorporated into a liquid paint or coating which would release the compound to the underlying substrate to control microbial growth or into the adjacent environment, for example as a marine anti-fouling agent.

The above liquid and solid embodiments may also include stabilizers to keep the compound unchanged during storage or other compounds to enhance its activity.

In many instances, a delivery agent herein can be a co-formulant. In many instances, a composition herein can comprise a compound as described herein, such as N-methyl N-nitroso isobutyramide, and a co-formulant. Examples of co-formulants include, but are not limited to: a water soluble pesticide, such as an herbicide, fungicide, insecticide, and plant growth regulant; an antifreeze agent, such as ethylene glycol, propylene glycol, glycerine, and urea; an antifoam agent, such as silicon; a suspending agent, such as silica, and MgSO4; a thickener, such as clay, polyvinyl alcohol, polyvinyl-pyrrolidone, and polyacrylamide; a preservative, such as formaldehyde, methyl or propyl parahydroxybenzoate, and sodium benzoate; a surfactant, such as a dispersing agent and a wetting agent; a buffer for pH stabilization, and many types of inert ingredient commonly used in agricultural compositions.

In some instances, the compositions herein can be formed as emulsifiable concentrates, soluble liquids, capsule suspensions, invert emulsions or wettable powders. Other exemplary co-formulants include nonyl phenol ethoxylates (NPE), toluene, xylene, and chlorinated solvents.

In applications in which the compound must be dispersed over time or space it is combined with an active carrier. As used herein, the term active carrier means a carrier that it suitable for dispersing the compound over space or time. Examples of active carriers are propellants as described above (that disperse the compound over space) and time release systems that release the compound continuously over time at a certain level, for example, from a microencapsulation system or diffusion out of a solid matrix. Active carriers do not include carriers that only allow for passive diffusion over space or non-controlled diffusion over time, such as combination with a saline solution for injection into or oral administration to a human or animal subject.

Kits or compositions comprising a compound herein can be prepared by known techniques to form emulsions, aerosols, sprays, or other liquid preparations, dusts, powders or solid preparations. These types of formulations can be prepared, for example, by combining with pesticide dispersible liquid carriers and/or dispersible solid carriers known in the art and optionally with carrier vehicle assistants, for example conventional pesticide surface-active agents, including emulsifying agents and/or dispersing agents.

Non-limiting examples of carriers include liquid carriers, including aerosol propellants which are gaseous at normal temperatures and pressures, such as Freon; inert dispersible liquid diluent carriers, including inert organic solvents, such as aromatic hydrocarbons (for example, benzene, toluene, xylene, alkyl naphthalenes), halogenated especially chlorinated, aromatic hydrocarbons (for example, chloro-benzenes), cycloalkanes (for example, cyclohexane), paraffins (for example, petroleum or mineral oil fractions), chlorinated aliphatic hydrocarbons (for example, methylene chloride, chloroethylenes), alcohols (for example, methanol, ethanol, propanol, butanol, glycol), as well as ethers and esters thereof (for example, glycol monomethyl ether), amines (for example, ethanolamine), amides (for example, dimethyl sormamide), sulfoxides (for example, dimethyl sulfoxide), acetonitrile, ketones (for example, acetone, methyl ethyl ketone, methyl isobutyl ketone, cyclohexanone), and/or water; as well as inert dispersible finely divided solid carriers such as ground natural minerals (for example, kaolins, clays, vermiculite, alumina, silica, chalk, calcium carbonate, talc, attapulgite, montmorillonite, kieselguhr), and ground synthetic minerals (for example, highly dispersed silicic acid, silicates).

Spreader and sticking agents, such as carboxymethyl cellulose, natural and synthetic polymers (for example, gum arabic, polyvinyl alcohol, and polyvinyl acetate), can also be used in as a delivery agent. Examples of commercial spreaders and sticking agents which can be used in the formulations include, but are not limited to, Schercoat™ P110, Pemulen™ TR2, and Carboset™ 514H, Umbrella™, Toximul™ 858 and Latron™ CS-7.

The compounds herein can be delivered in kits with a variety of different devices and systems. A delivery device is any device suitable to provide the compound to a locus in which it may contact the target pathogen. An exemplary delivery device is a pressurized container that can be filled with the compositions described herein. A kit may comprise the container and the composition.

In some embodiments, the delivery device is an aerosol delivery device, or a drip irrigation system, or an injection device, such as a soil injection device including an injection shank, or a device suitable for injection into wall cavities of an existing building structure. In other embodiments, the delivery device comprises a sprayer, such as a spray hose, spray can, or spray gun. This embodiment could be a mist or aerosol released by a fogging or spray stem or may be fine droplets release by a hydraulic sprayer. In another embodiment, the sprayer could be a pressurized can or vessel. In some embodiments, the compound may be delivered as a gas by a device in which it vaporizes in the delivery chamber of a fumigation system which can then distribute it as a gas through a container or structure.

Delivery methods and systems for a composition herein include, but are not limited to: fogging (liquid based); dips; microencapsulation (coat surface of slow release); solid matrix in package (film/tape); smart packaging (control preservation of food); aerosol format (on demand with propellant); granular (for example, to work into soil and release); injection into soil (for example, through a shanking method) and cover (for example, tarping) soil for few weeks.

Exemplary delivery systems include controlled-release delivery systems. Some controlled release delivery systems can reduce, for example, evaporation, leaching, ultraviolet light degradation, and soil degradation. In some instances, the compounds can be delivered by a microcapsule, microparticles, granules or macrodevices (for example, laminates, sheeting, tubes, and films). In an embodiment, the composition or kit is a sprayable ready-to-use (RTU) formulation suitable, for example, for delivery by fogging, aerosol spraying, and pump spraying methods for application in a variety of environments.

Screening Methods

The compositions of the present invention may also be used to screen for compounds that have activity against particular pathogens that are important in a certain application. For example, in one embodiment one could screen compounds for biocidal activity by preparing compounds of Formula 2, varying the R1 and R2 groups and testing the various analogs for activity against targets (pathogens or pests) of interest. The R1 and R2 groups are varied so that they are each independently hydrogen or an alkyl, haloalkyl, heteroalkyl, heterocycloalkyl, halocycloalkyl, cycloalkyl, heteroalkynyl, haloalkynyl, alkynyl, haloalkenyl, heteroalkenyl or alkenyl group.

In one screening method, the R2 group is held constant as a methyl group and only the R1 group is varied. In one embodiment, the R2 group is a methyl group and the R1 group is varied and may be alkyl, haloalkyl, cycloalkyl, or heteroalkyl, wherein the heteroatom is not sulfur. In yet another embodiment the R2 group is a methyl group and the R1 group is varied and is one of the compounds listed in Table 1A, above.

In one embodiment, the compounds are screened for biocidal activity at application rates that are at least within the various ranges described above for various applications; e.g., between about 0.5 mg/L soil to about 70.0 mg/L soil or between about 2 ug/L air to about 50 ug/L air.

In another embodiment the application of interest is crop protection and the pathogens of interest are one or more of the soil-borne pathogens and/or pests listed above for this field. In yet another embodiment, the application is food safety and the pathogens of interest are one or more of the food-borne pathogens or pests listed above.

In yet another embodiment, the application is protection of buildings or non-food materials, such as books and artwork, and the pathogens of interest are one or more of the pathogens and/or pests that affect buildings and goods such as books, artwork and clothing.

In yet another embodiment, the application is sanitization of medical and veterinary equipment and the pathogens of interest are one or more of the microorganisms that adversely affect human health, as listed above.

EXAMPLES

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 1

The possibility of a chiral molecule produced by *Muscodor albus* was explored since 2-methyl-1-butanol can exist as a pair of enantiomers. From previous experiments, it was also known that 3-methyl-1-butanol was produced by the fungi but there was no clear evidence if there was preference for either alcohol and the ratio by which they were being produced.

By using GC-MS analysis in conjunction with solid-phase micro-extraction (SPME) and a Supelco Beta DEX-225 (30 m×0.24 mm×0.25 μm) chiral column, it was determined that (S)-(−)-2-methyl-1-butanol and 3-methyl-1-butanol were being produced in 1:1 ratio. This was the first evidence that both compounds were produced by *Muscodor albus*. However, further experiments demonstrated that neither compound by itself nor the compounds in combination are sufficient to provide the biological control of the rye formulation. Therefore, the compounds are most likely not primarily responsible for the bioactivity of *M. albus*. Example 2 illustrates methods herein of describing the discovery of active compounds from *M. albus.*

Example 2

Identification by mass spectrometry (MS) and nuclear magnetic resonance (NMR). MS data was accumulated in-house at AgraQuest and contract MS Lab at Iowa State University. NMR data was obtained from contract lab at Acorn, Inc.

In order to answer a question as to whether there was an unidentified component of VOCs emitted from *M. albus*, the following experiment was conducted. First, 3 spawn bags of fresh and actively growing *Muscodor albus* on rye grain (900 g each) were transferred to a 20-L carboy adapted with a nipple at the base of the flask to allow for passage of filtered air into the carboy. The top opening of the carboy was adapted with a one-hole rubber stopper. One end of a piece of silicone tubing was then connected to the rubber stopper at the top of the carboy and the other end connected to a Supelco polyurethane foam (PUF) cartridge containing XAD2 resin. Optionally, sequential cold traps were used to trap as much vapor water as possible before reaches the resin cartridge. As filtered air was passed through the bottom nipple of the carboy, the organic volatiles compounds produced by the fungi were flushed onto the PUF-XAD2 cartridge and absorbed onto the resin. The flow rate used in this example was 2 L/min. The Supelco PUF/XAD2 tubes are rated to work at up to a 1 to 5 L/min air flow rate. After 4 hrs, the air flow was stopped and the cartridge removed from the system. Then the cartridge was rinsed with absolute ethanol (10 mL) and the ethanol eluate evaluated for activity against *Penicillium* expansum on potato dextrose agar (PDA) plates or *Rhizoctonia solani* in soil. This procedure was repeated several times and the ethanol eluate was performing at comparable levels of biological control as the microbial formulation of *Muscodor albus* on rye grain at comparable concentrations (ug VOCs/L air or mg VOCs/L soil).

The trapping of the volatiles from *Muscodor* was extended to shake flask fermentations and bioreactors in which the resin Amberlite XAD2 (other resins such as Amberlite XAD4, Amberlite XAD 16, Diaion HP-20, Sepabeads SP-207, Dowex Optipore SD-2 and charcoal were also successfully used to trap the VOCs) was used to trap and elute the VOC with ethanol.

This ethanol eluate was further examined by GC-MS and it was found an unknown peak with retention time (Rt=8.54 min) not previously detected when using direct headspace and SPME fiber or coated stir bars; for example, the Twister from Gerstel, Inc. Further evaluation of the ethanol eluate confirmed that the unknown peak (Compound 1) was heat sensitive and the standard injection temperature (220° C.) used for previous analysis in the GC was decomposing Compound 1 into isobutyric acid (IBA) and, presumably, some other undetected byproduct. It was also found that Compound 1 was unstable to high pH (above pH 7).

The ethanol eluate was submitted for High Resolution Mass Spectrometry in both electron impact (EI) and chemical ionization (CI) in both positive and negative mode to determine the chemical composition of Compound 1. See Table 2.

TABLE 2

High resolution MS results using on-column cooled injection of ethanol eluate

| MS Technique | Mode | Gas Reagent used | Observed mass | Calculated formula |
| --- | --- | --- | --- | --- |
| EI (on-column cooled injection) | Positive | | 130.0748 | $C_5H_{10}N_2O_2$ |
| CI (on-column cooled injection) | Positive | Methane | 131.0828 | $C_5H_{11}N_2O_2$ |
| CI (on-column cooled injection) | Negative | Methane | 129.0714 | $C_5H_9N_2O_2$ |

To fully determine the structure of Compound 1, a preparative fraction collection unit was acquired from Gerstel, Inc. and adapted to a GC unit with a Peltier cooling injection unit. Multiple injections were performed and the peak corresponding to Compound 1 was collected in sufficient quantity for NMR structure elucidation. Table 3 shows the proton and $^{13}C$ chemical shifts for the structure of Compound 1 compared to synthetic N-methyl isobutyramide. Synthesis of this compound is described below.

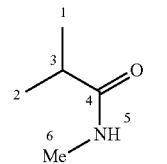

N-methylisobutyramide (Compound 1)

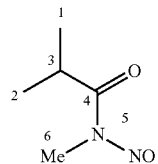

N-methyl-N-nitrosoisobutyramide

TABLE 3

NMR assignment for Compound 1 compared to N-methyl isobutyramide.

| | N-Methyl isobutyramide | | Compound 1 | |
| --- | --- | --- | --- | --- |
| Position | δH | δC | δH | δC |
| 1 | 1.047, d (J = 7.2) | 19.81 | 1.29, d (J = 6.8) | 19.41 |
| 2 | 1.047, d (J = 7.2) | 19.29 | 1.29, d (J = 6.8) | 19.41 |
| 3 | 2.42, m | 35.7 | 3.90, m | 33.41 |
| 4 | | 179.7 | | 181 |
| 5 | 5.32, broad s | | | |
| 6 | 2.68, s | 26.1 | 3.06, s | 25.67 |

The structure of Compound 1 was further confirmed as N-methyl N-nitroso isobutyramide by chemical synthesis. Treatment of N-Methyl isobutyramide with $NaNO_2$ (sodium nitrite) in acetic acid-acetic anhydride at 0° C. yielded Compound 1. GC retention time and mass fragmentation pattern matches those observed for Compound 1 obtained from volatile trapping experiments.

Example 3

Procedure A: A solution of an amide (Formula 1 in Procedure A) (0.10 mole) in a mixture of acetic acid (10 ml) and acetic anhydride (50 ml) is cooled to 0° C. and 15 grams of granular sodium nitrite (0.22 moles) is added over 5 hours. After 10 hours at 0° C. the temperature is allowed to rise to 10-15° C. for 30 minutes and the mixture is poured into a mixture of ice and water. The nitrosoamide (Formula 2) is extracted with ether, and the upper phase is washed with water, with an aqueous solution of sodium carbonate (5%), with water, and then dried with anhydrous sodium sulfate. The solvent is removed (under vacuum), and depending on the properties of the nitrosoamide (Formula 2), the product is either distilled under vacuum in a temperature less than 40° C., or recrystallized from ether-pentane mixtures.

Example 4

A solution of the amide (0.10 mole):

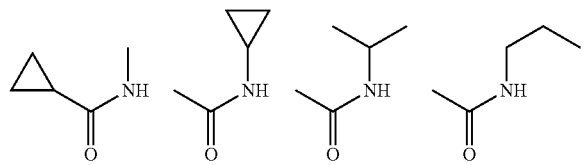

in a mixture of acetic acid (10 ml) and acetic anhydride (50 ml) is cooled to 0° C. and 15 grams of granular sodium nitrite (0.22 moles) is added over 5 hours. After 10 hours at 0° C. the temperature is allowed to rise to 10-15° C. for 30 minutes and the mixture is poured into a mixture of ice and water.

The nitrosoamide:

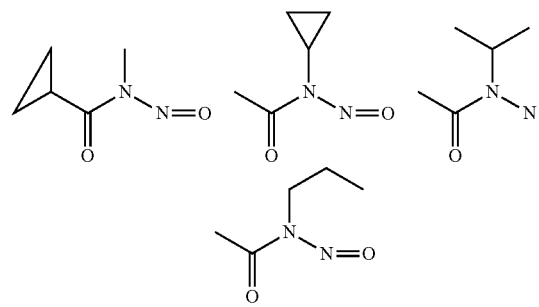

is extracted with ether, and the upper phase is washed with water, with an aqueous solution of sodium carbonate (5%), with water, and then dried with anhydrous sodium sulfate. The solvent is removed (under vacuum), and depending on the properties of the nitrosoamide, the product is either distilled under vacuum in a temperature less than 40° C., or recrystallized from ether-pentane mixtures.

Example 5

A solution of the amide (0.10 mole):

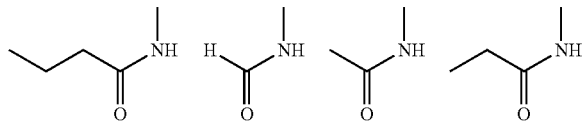

in a mixture of acetic acid (10 ml) and acetic anhydride (50 ml) is cooled to 0° C. and 15 grams of granular sodium nitrite (0.22 moles) is added over 5 hours. After 10 hours at 0° C. the temperature is allowed to rise to 10-15° C. for 30 minutes and the mixture is poured into a mixture of ice and water.

The nitrosoamide:

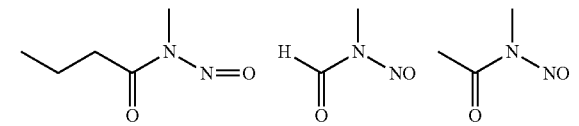

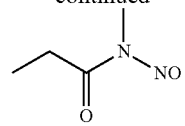

is extracted with ether, and the upper phase is washed with water, with an aqueous solution of sodium carbonate (5%), with water, and then dried with anhydrous sodium sulfate. The solvent is removed (under vacuum), and depending on the properties of the nitrosoamide, the product is either distilled under vacuum in a temperature less than 40° C., or recrystallized from ether-pentane mixtures.

Example 6

A solution of the amide (0.10 mole):

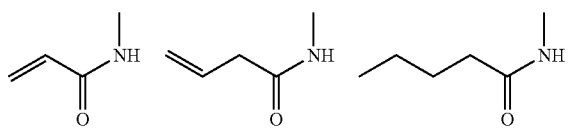

in a mixture of acetic acid (10 ml) and acetic anhydride (50 ml) is cooled to 0° C. and 15 grams of granular sodium nitrite (0.22 moles) is added over 5 hours. After 10 hours at 0° C. the temperature is allowed to rise to 10-15° C. for 30 minutes and the mixture is poured into a mixture of ice and water.

The nitrosoamide:

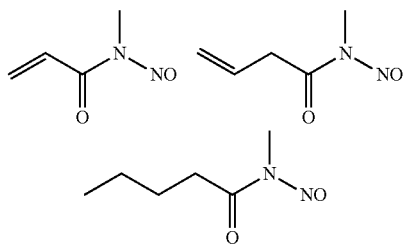

is extracted with ether, and the upper phase is washed with water, with an aqueous solution of sodium carbonate (5%), with water, and then dried with anhydrous sodium sulfate. The solvent is removed (under vacuum), and depending on the properties of the nitrosoamide, the product is either distilled under vacuum in a temperature less than 40° C., or recrystallized from ether-pentane mixtures.

Example 7

A solution of the amide (0.10 mole):

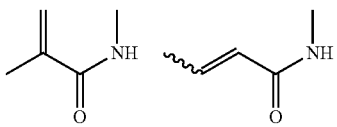

-continued

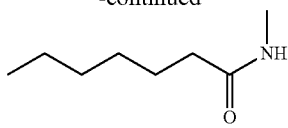

in a mixture of acetic acid (10 ml) and acetic anhydride (50 ml) is cooled to 0° C. and 15 grams of granular sodium nitrite (0.22 moles) is added over 5 hours. After 10 hours at 0° C. the temperature is allowed to rise to 10-15° C. for 30 minutes and the mixture is poured into a mixture of ice and water.

The nitrosoamide:

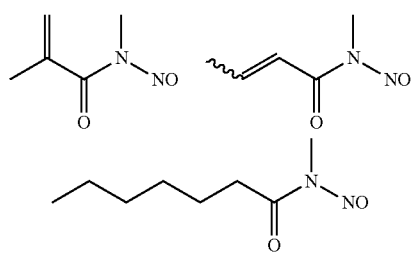

is extracted with ether, and the upper phase is washed with water, with an aqueous solution of sodium carbonate (5%), with water, and then dried with anhydrous sodium sulfate. The solvent is removed (under vacuum), and depending on the properties of the nitrosoamide, the product is either distilled under vacuum in a temperature less than 40° C., or recrystallized from ether-pentane mixtures.

Example 8

A solution of the amide (0.10 mole):

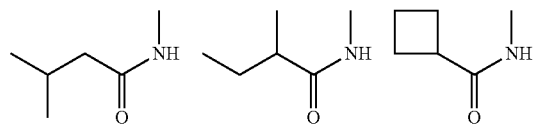

in a mixture of acetic acid (10 ml) and acetic anhydride (50 ml) is cooled to 0° C. and 15 grams of granular sodium nitrite (0.22 moles) is added over 5 hours. After 10 hours at 0° C. the temperature is allowed to rise to 10-15° C. for 30 minutes and the mixture is poured into a mixture of ice and water.

The nitrosoamide:

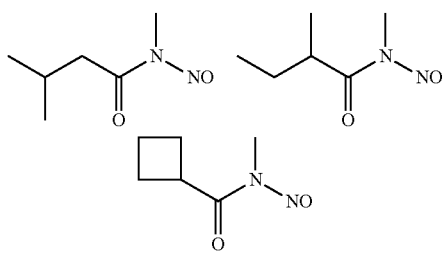

is extracted with ether, and the upper phase is washed with water, with an aqueous solution of sodium carbonate (5%), with water, and then dried with anhydrous sodium sulfate. The solvent is removed (under vacuum), and depending on the properties of the nitrosoamide, the product is either distilled under vacuum in a temperature less than 40° C., or recrystallized from ether-pentane mixtures.

Example 9

A solution of the amide (0.10 mole):

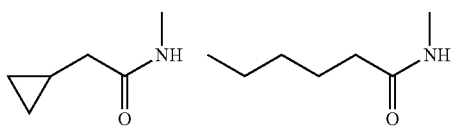

in a mixture of acetic acid (10 ml) and acetic anhydride (50 ml) is cooled to 0° C. and 15 grams of granular sodium nitrite (0.22 moles) is added over 5 hours. After 10 hours at 0° C. the temperature is allowed to rise to 10-15° C. for 30 minutes and the mixture is poured into a mixture of ice and water.

The nitrosoamide:

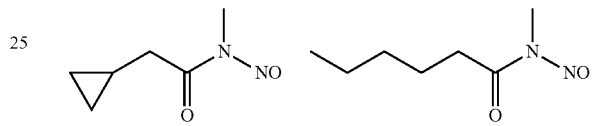

is extracted with ether, and the upper phase is washed with water, with an aqueous solution of sodium carbonate (5%), with water, and then dried with anhydrous sodium sulfate. The solvent is removed (under vacuum), and depending on the properties of the nitrosoamide, the product is either distilled under vacuum in a temperature less than 40° C., or recrystallized from ether-pentane mixtures.

Example 10

A solution of the amide (0.10 mole):

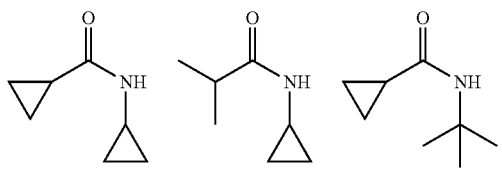

in a mixture of acetic acid (10 ml) and acetic anhydride (50 ml) is cooled to 4° C. and 15 grams of granular sodium nitrite (0.22 moles) is added over 5 hours. After 10 hours at 4° C. the temperature is allowed to rise to 10-15° C. for 30 minutes and the mixture is poured into a mixture of ice and water.

The nitrosoamide:

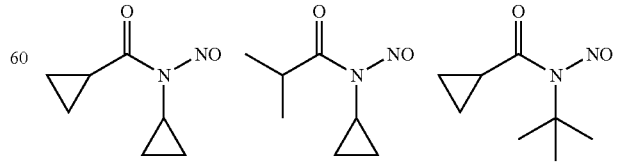

is extracted with ether, and the upper phase is washed with water, with an aqueous solution of sodium carbonate (5%), with water, and then dried with anhydrous sodium sulfate. The solvent is removed (under vacuum), and depending on the properties of the nitrosoamide, the product is either distilled under vacuum in a temperature less than 40° C., or recrystallized from ether-pentane mixtures.

Example 11

A solution of the amide (0.10 mole):

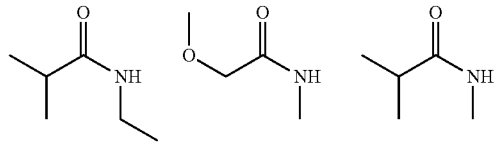

in a mixture of acetic acid (10 ml) and acetic anhydride (50 ml) is cooled to 4° C. and 15 grams of granular sodium nitrite (0.22 moles) is added over 5 hours. After 10 hours at 4° C. the temperature is allowed to rise to 10-15° C. for 30 minutes and the mixture is poured into a mixture of ice and water.

The nitrosoamide:

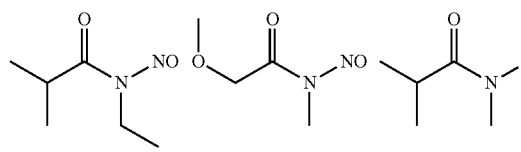

is extracted with ether, and the upper phase is washed with water, with an aqueous solution of sodium carbonate (5%), with water, and then dried with anhydrous sodium sulfate. The solvent is removed (under vacuum), and depending on the properties of the nitrosoamide, the product is either distilled under vacuum in a temperature less than 40° C., or recrystallized from ether-pentane mixtures.

Example 12

A solution of the amide (0.10 mole):

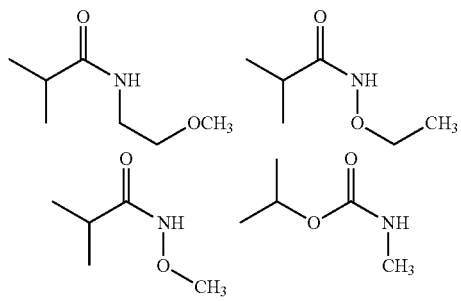

in a mixture of acetic acid (10 ml) and acetic anhydride (50 ml) is cooled to 4° C. and 15 grams of granular sodium nitrite (0.22 moles) is added over 5 hours. After 10 hours at 4° C. the temperature is allowed to rise to 10-15° C. for 30 minutes and the mixture is poured into a mixture of ice and water.

The nitrosoamide:

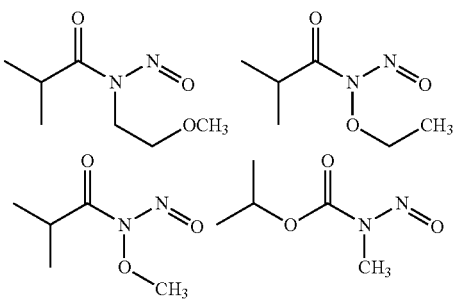

is extracted with ether, and the upper phase is washed with water, with an aqueous solution of sodium carbonate (5%), with water, and then dried with anhydrous sodium sulfate. The solvent is removed (under vacuum), and depending on the properties of the nitrosoamide, the product is either distilled under vacuum in a temperature less than 40° C., or recrystallized from ether-pentane mixtures.

Example 13

A solution of the amide (0.10 mole):

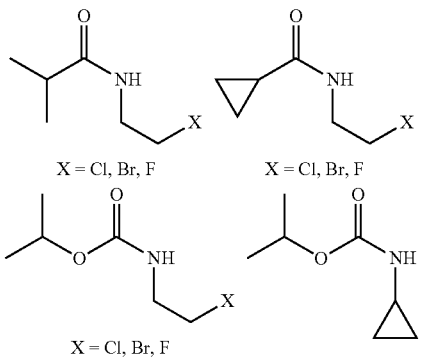

X = Cl, Br, F in a mixture of acetic acid (10 ml) and acetic anhydride (50 ml) is cooled to 4° C. and 15 grams of granular sodium nitrite (0.22 moles) is added over 5 hours. After 10 hours at 4° C. the temperature is allowed to rise to 10-15° C. for 30 minutes and the mixture is poured into a mixture of ice and water.

The nitrosoamide:

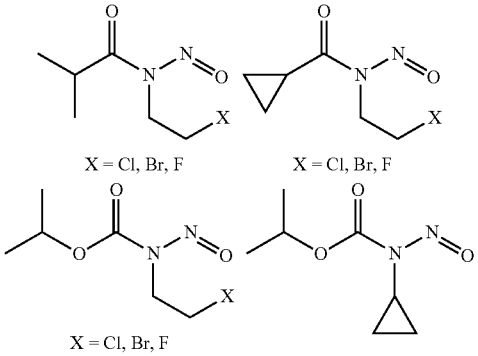

X = Cl, Br, F is extracted with ether, and the upper phase is washed with water, with an aqueous solution of sodium carbonate (5%), with water, and then dried with anhydrous sodium sulfate. The solvent is removed (under vacuum), and depending on the properties of the nitrosoamide, the product is either distilled under vacuum in a temperature less than 40° C., or recrystallized from ether-pentane mixtures.

Example 14

A solution of the amide (0.10 mole):

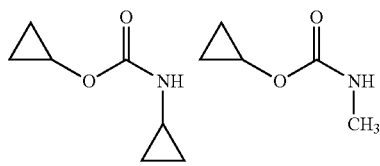

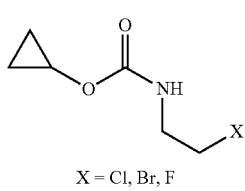

X = Cl, Br, F in a mixture of acetic acid (10 ml) and acetic anhydride (50 ml) is cooled to 4° C. and 15 grams of granular sodium nitrite (0.22 moles) is added over 5 hours. After 10 hours at 4° C. the temperature is allowed to rise to 10-15° C. for 30 minutes and the mixture is poured into a mixture of ice and water.

The nitrosoamide:

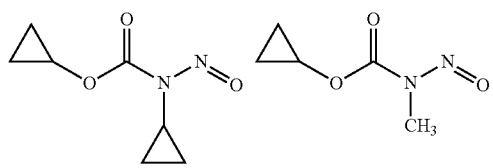

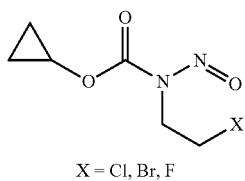

X = Cl, Br, F is extracted with ether, and the upper phase is washed with water, with an aqueous solution of sodium carbonate (5%), with water, and then dried with anhydrous sodium sulfate. The solvent is removed (under vacuum), and depending on the properties of the nitrosoamide, the product is either distilled under vacuum in a temperature less than 40° C., or recrystallized from ether-pentane mixtures.

Example 15

A solution of the amide (0.10 mole):

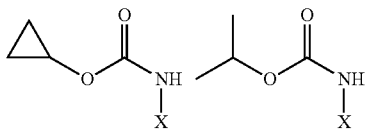

X=ethyl, propyl, isopropyl, tert-butyl X=ethyl, propyl, isopropyl, tert-butyl in a mixture of acetic acid (10 ml) and acetic anhydride (50 ml) is cooled to 0° C. and 15 grams of granular sodium nitrite (0.22 moles) is added over 5 hours. After 10 hours at 0° C. the temperature is allowed to rise to 10-15° C. for 30 minutes and the mixture is poured into a mixture of ice and water.

The nitrosoamide:

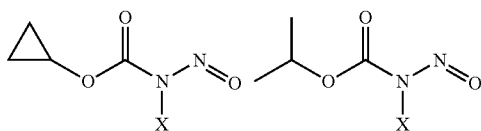

X=ethyl, propyl, isopropyl, tert-butyl X=ethyl, propyl, isopropyl, tert-butyl is extracted with ether, and the upper phase is washed with water, with an aqueous solution of sodium carbonate (5%), with water, and then dried with anhydrous sodium sulfate. The solvent is removed (under vacuum), and depending on the properties of the nitrosoamide, the product is either distilled under vacuum in a temperature less than 40° C., or recrystallized from ether-pentane mixtures.

Example 16

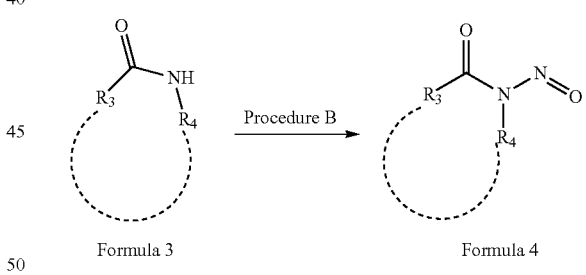

Formula 3     Procedure B     Formula 4

$R_3$ and $R_4$ are each independently an alkyl, haloalkyl, or alkenyl group.

Procedure B: A solution of the amide (Formula 3) (0.10 mole) in a mixture of acetic acid (10 ml) and acetic anhydride (50 ml) is cooled to 0° C. and 15 grams of granular sodium nitrite (0.22 moles) is added over 5 hours. After 10 hours at 0° C. the temperature is allowed to rise to 10-15° C. for 30 minutes and the mixture is poured into a mixture of ice and water. The nitrosoamide (Formula 4) is extracted with ether, and the upper phase is washed with water, with an aqueous solution of sodium carbonate (5%), with water, and then dried with anhydrous sodium sulfate. The solvent is removed (under vacuum), and depending on the properties of the nitrosoamide (Formula 4), the product is either distilled under vacuum in a temperature less than 40° C., or recrystallized from ether-pentane mixtures.

The compounds in the table below are synthesized according to Procedure B.

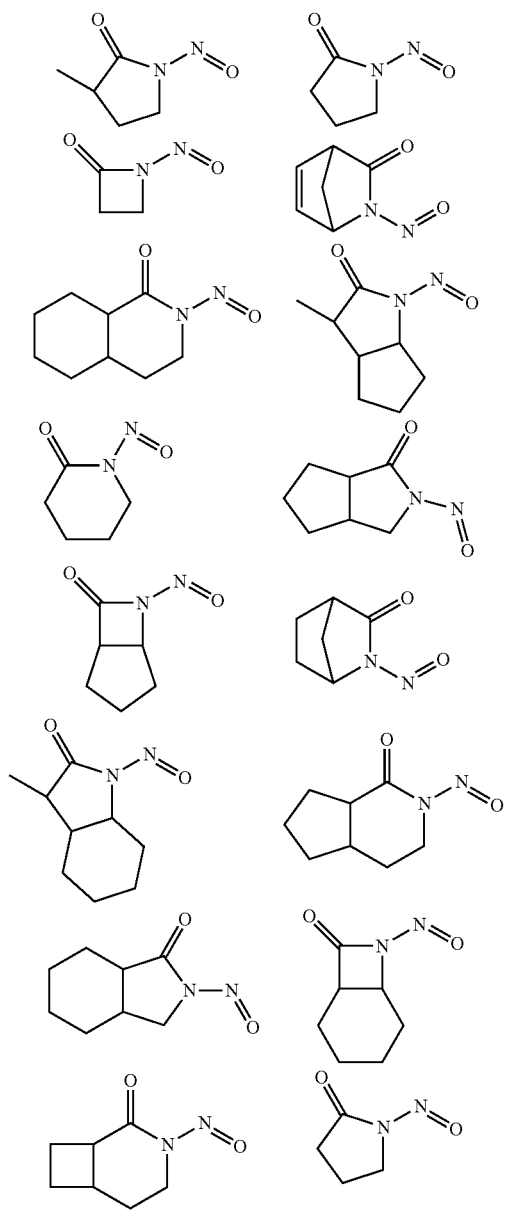

Example 17

Building molds can be inhibited in vitro by the compounds herein and VOCs from *Muscodor albus*. In a box fumigation test, PDA plates with plugs of test organisms in (3 plugs/isolate) are fumigated for 48 h in 11 L boxes containing 0, 10, 30, 50 or 100 g with a compound herein or a kit comprising the compound herein. The plates are then taken out and assessed for growth. Plugs which do not show sign of growth are transferred to fresh PDA to assess their viability. There may be a wide range in sensitivity to the compounds among building molds, for example while some species are killed readily, several might resist some concentrations in the lower range of delivery. Therefor; depending on the results of the experiments, some organisms are retested.

Many species of molds are highly sensitive to the compounds and kits herein. Molds that are tested for inhibition by the compounds herein are: *Acremonium strictum, Alternaria alternata, Aspergillus flavus, Aspergillus fumigatus, Aspergillus niger, Aspergillus ochraceus, Aspergillus sydowii, Aspergillus ustus, Aspergillus versicolor, Chaetomium globosum, Cladosporium cladosporioides, Eurotium amstelodami, Paecilomyces variotii, Penicillium brevi-compactum, Penicillium chrysogenum, Penicillium citrinum, Penicillium expansum, Penicillium roquefortii, Scopulariopsis brevicaulis, Stachybotrys chartarum, Trichoderma viride, Ulocladium botrytis*, and *Wallemia sebi*.

Example 18

Experiments were conducted for the use of an ethanol eluate from the VOCs of *Muscodor albus* as obtained from the methods described herein for soil damping-off against *Rhizoctonia*. For all damping-off experiments, the following experimental design was followed:

For soil experiments, garden soil (sandy loam) mixed with 20% vermiculite by volume was adjusted to a moisture level of 7 on the Soil Moisture Meter®. For potting mix experiments, potting mix was moistened with 150 ml DI water/L mix. The mix was infested by adding 8 g of vermiculite culture of *Rhizoctonia solani* per liter of mix (the non-infested treatment is removed prior to infestation). The mix was then distributed among square 500-ml plastic pots, providing sufficient pots for four pots per treatment. Each pot in a volatile treatment was placed inside a plastic bag to simulate tarping. After 48 hours, all pots were removed from the plastic bags and allowed to stand at room temperature for 1-2 hours. After the incubation period, each pot was planted with approximately 65 broccoli seeds and the seeds were covered with a small layer of potting mix. After planting, the pots were watered by placing them in a plastic tray with a layer of deionized water in the bottom and were allowed to soak in water for ~30 minutes. Watering was then performed as needed during the course of the experiment and avoiding dry or water-saturated mix. After approximately 7 days, normal seedlings were counted. Seedlings without a root system were not counted. Results were expressed as percent emergence, calculated from a potential of 65 seedlings for 100% emergence.

Figure 8:
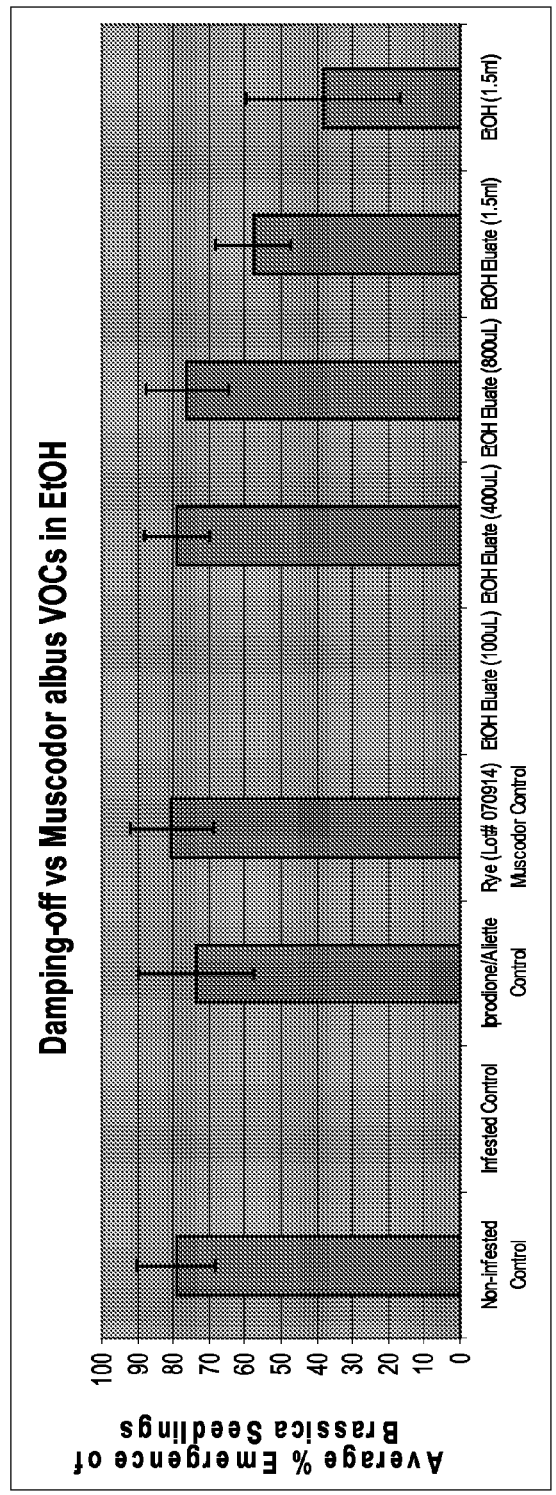

Additional experiments were run using Compound 1. The result of the damping-off study are summarized in FIG. 7, wherein NIC is a non-infested control, IC is infested control, Chemical is a tested control, Rye is a rye formulation from *M. albus*, EtOH is an ethanol eluate of VOCs from *M. albus*, and the rest are dose amounts of synthetic Compound 1 (wherein Compound 1 is N-methyl N-nitroso isobutyramide). The % emergence shown in FIG. 8 is the % emergence of *Brassica* seedlings when planted in soil previously infested with *Rhizoctonia* and then treated with the different mixtures or compounds. As demonstrated, synthetic N-methyl N-nitroso isobutyramide at varying doses is able to reduce the *Rhizoctonia* infection and allow *Brassica* seedlings to emerge from the soil. The dose units are milligrams of compound per liter soil. The effectiveness to allow the emergence of *Brassica* seedlings in contaminated soil as described in this example was also determined for VOCs eluted in ethanol and collected by the methods described. The results of this study are illustrated in FIG. 8.

Example 19

For all post-harvest apple experiments, the following experimental design was followed. Organic apples (bought from the Davis Food Co-op) were placed at room temperature in 11.4 L boxes, each held in a weighing dish to prevent rolling. The apples were inoculated 24 hours before treatment. For this, they were wounded with a 4 mm screw tip and inoculated with 15 µl of a spore suspension of *Penicillium expansum* (strain PENE.2, $2 \times 10^5$ conidia/ml in water+0.01% Tween 80) and incubated in the closed boxes. After 24 hours, the treatments were added to the boxes by drenching a Kimwipe with the EtOH carrier and placed in a weigh dish to volatilize in the box, which were then closed. Two *Penicillum expansum* plates (150 ul of PENE.2, $2 \times 10^5$ conidia/ml in water+0.01% Tween 80 evenly spread onto a PDA plate) were placed in each box at this time in order to test the effect on the pathogen alone. After a fumigation period of 24 h, the treatments were removed. The *P. expansum* plates were also removed and placed at room temperature to grow. These plates were evaluated after about 4 days of growth. These plates were rated on % germination based on the coverage of the PDA plate by a *P. expansum* lawn. An assessment of the apples was made 7 days after inoculation and percent infection was scored based on the number of infected fruit out of the total fruit.

Figure 9:
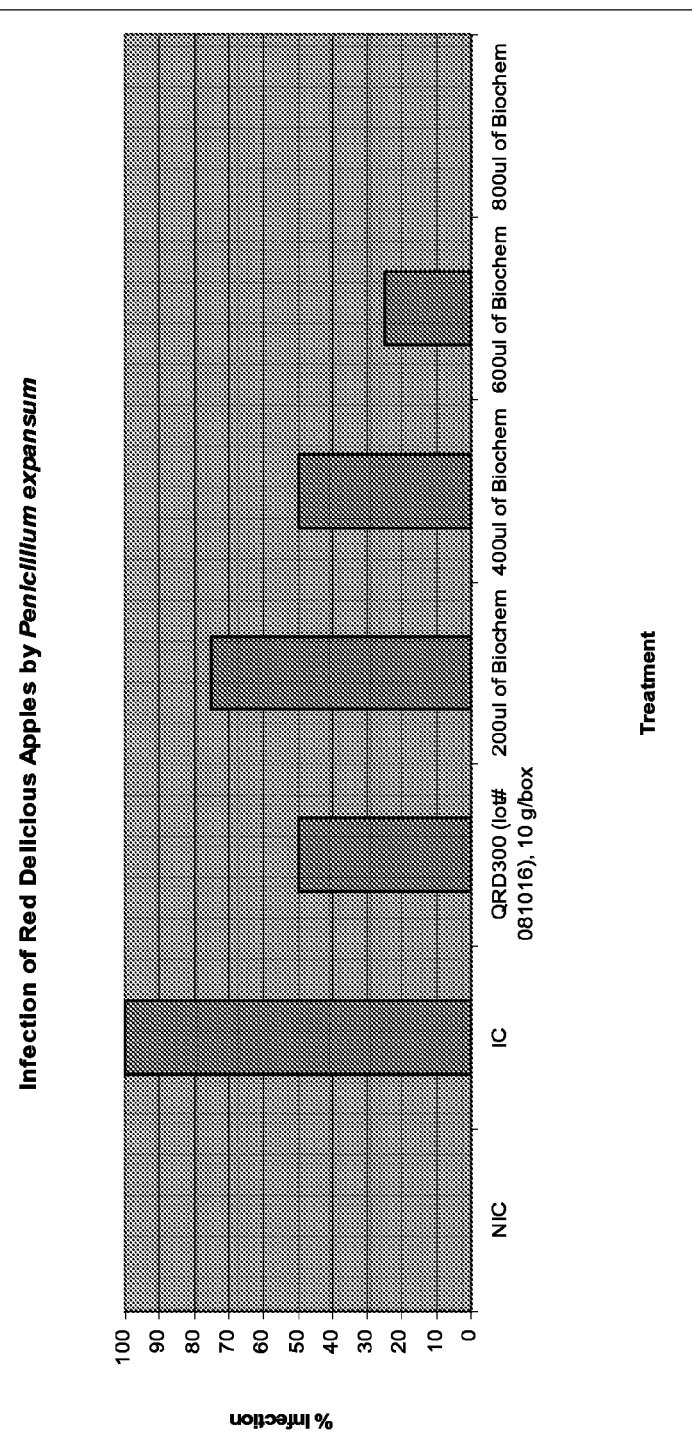
FIG. 9 illustrates the control of *P. expansum* in apples using a compound of the invention.

An 11 L box containing red delicious apples infected with *Penicillium expansum* was fumigated with a solution comprising 0.915 mg N-methyl N-nitroso isobutyramide per mL solution. The severity of the infection of the apples by *Penicillium expansum* was evaluated after treatment with the solution. The results of the treatment are demonstrated in FIG. 9, wherein "biochem" represents the solution and "NIC" is a non-infested control and "IC" is infested control with no treatment. As shown, using a higher concentration of N-methyl N-nitroso isobutyramide per volume of the air within the box, significantly improves removing the infection from the apples.

Example 20

For the post-harvest experiments with lemons, the following experimental design was followed. Organic lemons (bought from the Davis Co-op) were placed at room temperature in 11.4 L boxes. The lemons were inoculated 24 h before treatment. For this, they were wounded with a 4 mm screw tip and inoculated with 15 µl of spore suspension of *Penicillium digitatum* (strain PEND.1, $2 \times 10^5$ conidia/ml in water+0.01% Tween 80) and incubated in the closed boxes. After 3-24 h, the samples were added to the boxes, drenched on a Kimwipe and placed in a weight dish to volatilize in the box, which were then closed. Two *Penicillium expansum* plates (150 ul of PENE.2, $2 \times 10^5$ conidia/ml in water+0.01% Tween 80 evenly spread onto a PDA plate) were placed in each box at this time. Placing *P. expansum* plates in the lemon boxes allowed comparison of any potential absorbing effect of lemons on the treatments compared to apples (*P. expansum* plates were used in the apple experiment rather than *P. digitatum*). After a fumigation period of 24 h the treatments were removed, and the *P. expansum* plates were also removed and placed at room temperature to grow. These plates were evaluated after about 4 days of growth and were rated on % germination based on the coverage of the PDA plate by a *P. expansum* lawn. An assessment of the lemons was made 7 days after inoculation and percent infection was scored based on the number of infected fruit out of the total fruit.

Figure 10:
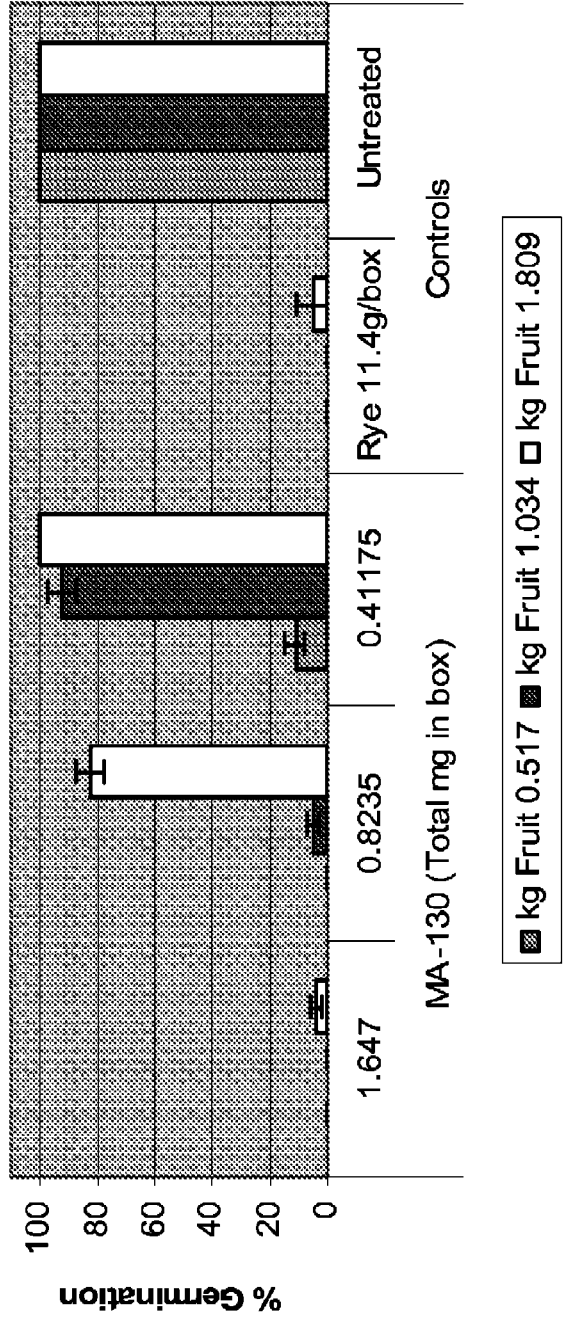
FIG. 10 shows the effect of fruit biomass on the control of *P. expansum* in lemons using a compound of the invention.
Figure 11:
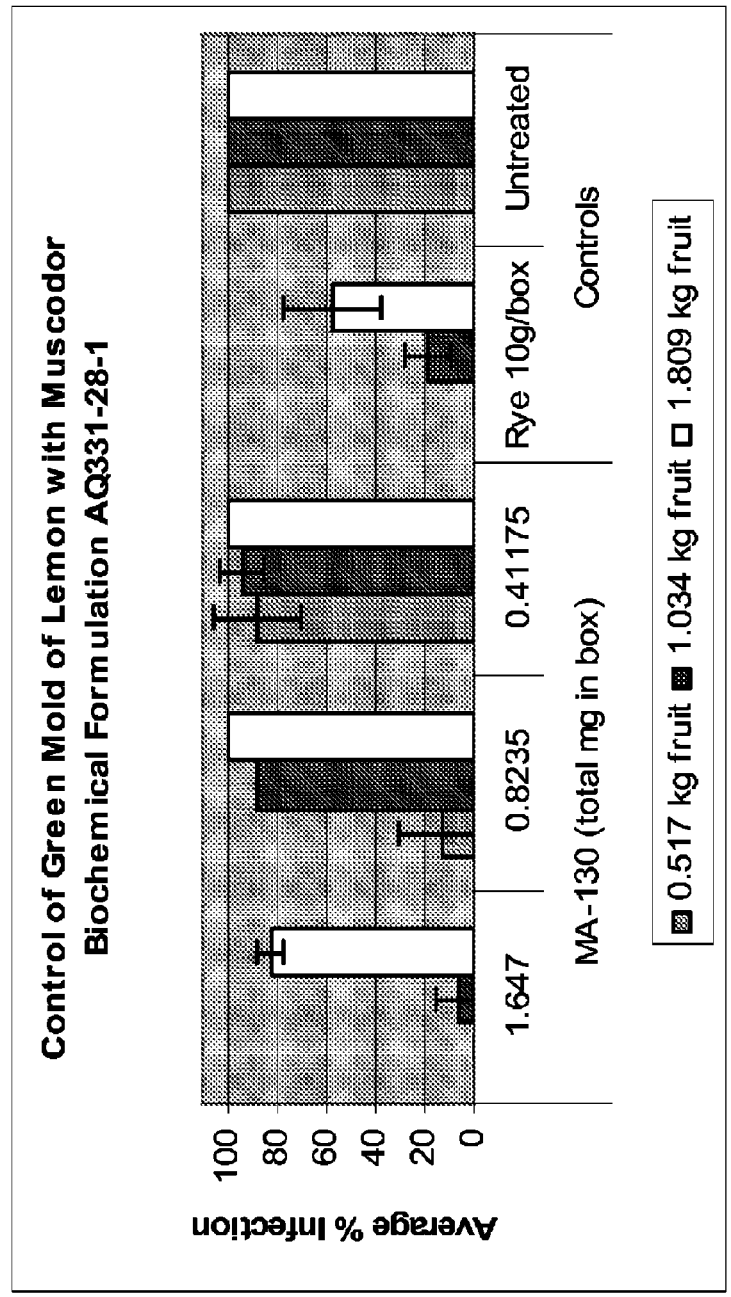
FIGS. 11 and 12 illustrate control of green mold (*P. digitatum*) in lemons.
Figure 12:
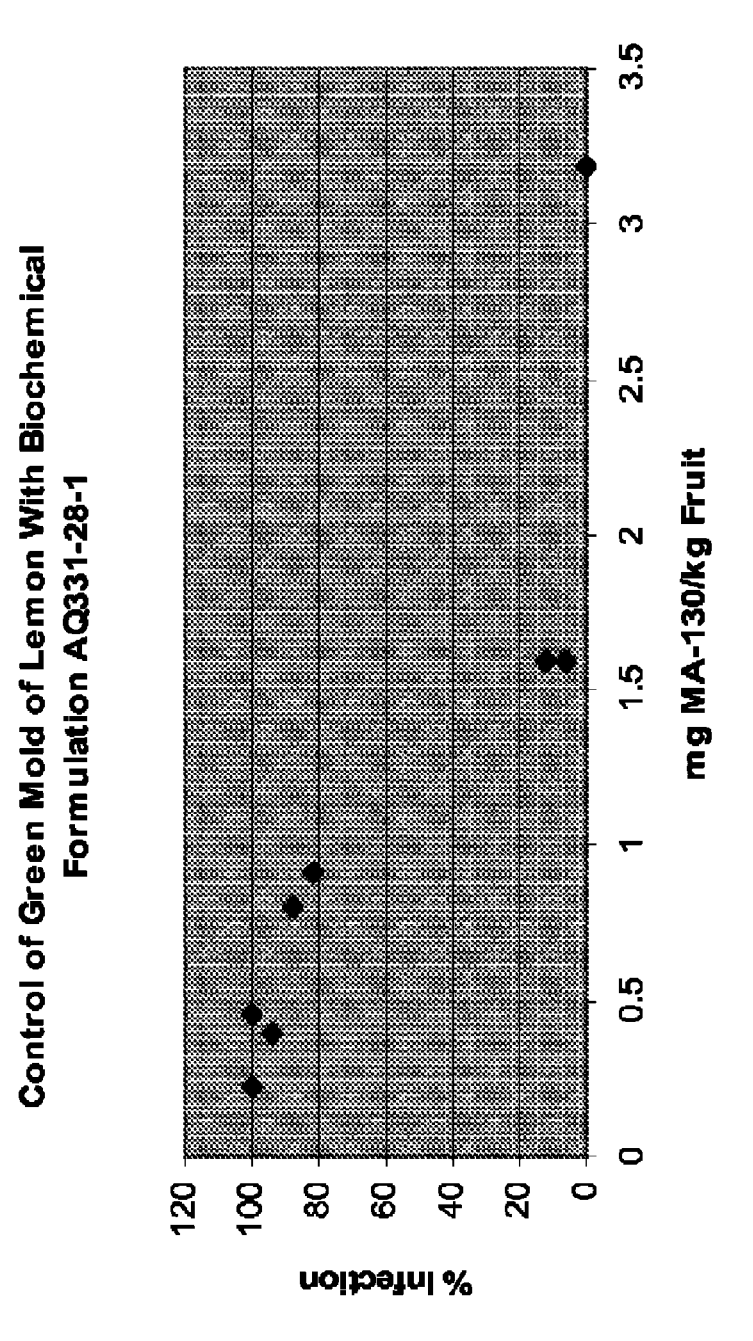

Treatments were performed on 4, 8, and 14 lemons collectively weighing 0.516, 1.034, and 1.809 kg, respectively, on average. Results of the study are shown in FIGS. 10, 11 and 12. The following samples are shown: 1) Untreated Control; 2) 11.4 g *Muscodor albus* rye culture (Lot #090325), rehydrated with 11.4 mL sterile, DI H2O; 3) Biochemical formulation amounts of 450, 900, and 1800 ul containing 0.412, 0.824, and 1.647 mg Compound 1, respectively. The biochemical formulation referred to here and in Example 19 refers to Compound 1 that was isolated from *Muscodor albus* as described in Example 2 and was not synthetically made. (Experiments were also conducted in which Compound 1, either synthesized or obtained by the isolation methods described in Example 2, was heat treated and then tested for activity. In either case, the biochemical formulation or the synthetic, the heat-treated Compound 1 lost activity after heat treatment.)

Example 21

Figure 13:
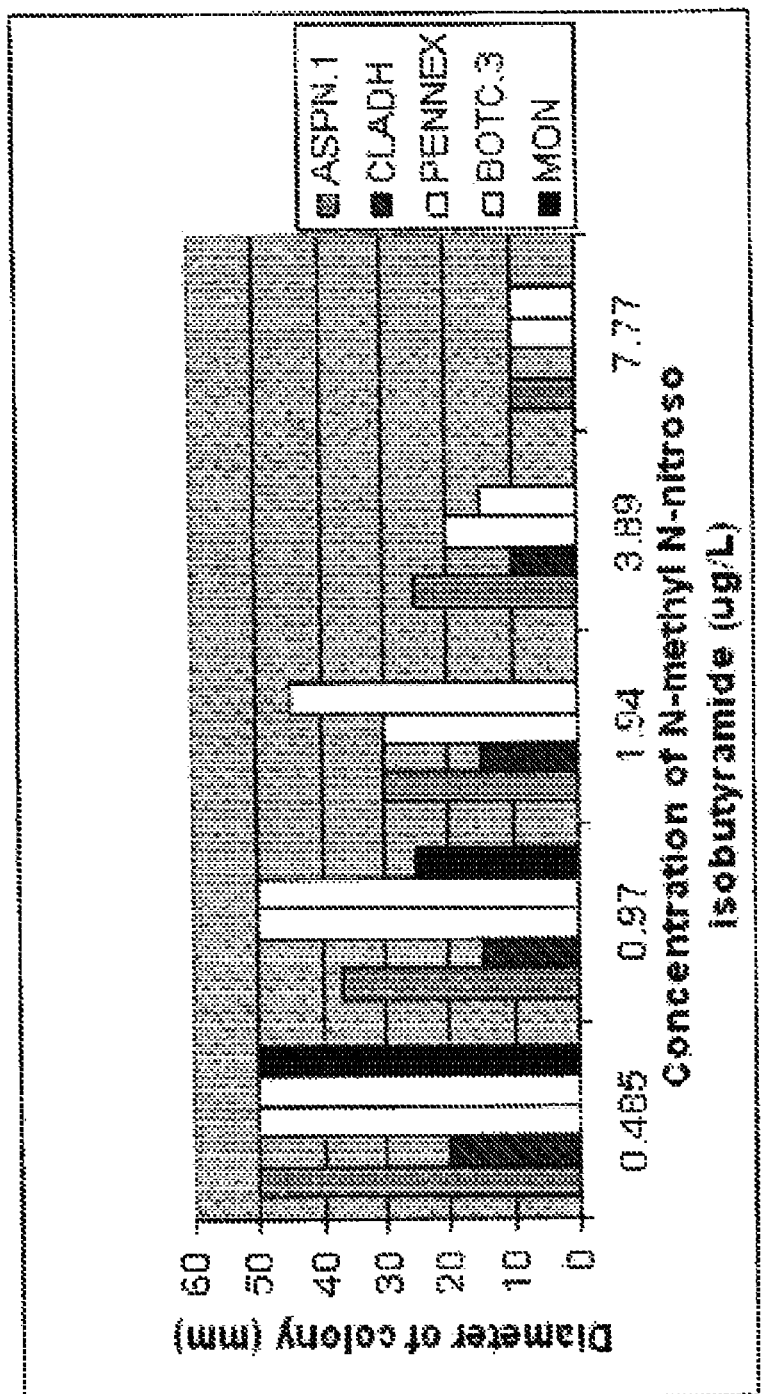
FIG. 13 illustrates the results from exposing five different fungal pathogens to different amounts of N-methyl N-nitroso isobutyramide in the method described in Example 13.

Agar plugs from a 7-14 day culture of each of the pathogens shown in FIG. 13 were removed from the actively growing plate and placed into the center of a 60 mm×15 mm potato dextrose agar plate. 5 plates were place into the 6-liter closed box with a fan. Different amounts of the N-methyl N-nitroso isobutyramide were added to the box on a filter paper taped to an aluminum weigh pan. The fans were turned on and the plates exposed to the volatiles for 24 hours. The plates were removed form the box and allowed to incubate at room temperature. The plates were monitored for growth after 2-5 days of incubation. (Time was dependent on the cultures—some grow faster than others). The diameter of the colony was measured in mm and compared to a control exposed to no volatiles.

Example 22

Experiments were conducted to determine the fungicidal activity of several compounds of the invention using *Penicillium expansum* as the test organism.

Plates of potato dextrose agar were streaked with a standard culture of *Penicillium expansum* spores (0.1 ml of a $2 \times 10^5$ cfu/ml) and placed in sealed plastic containers (nominal volume 6 liters). The containers (Rubbermaid) were fitted with a small fan (Radio Shack 12VDC) in the lids to ensure good distribution of the test compounds. The plates were exposed to different volumes (2.5 µl, 5 µl, 10 µl, 20 µl, 40 µl, 80 µl, or 120 µl) of standard solutions (1.0 to 4.0 mg/ml) of tested compounds in ethanol, under ambient conditions. After exposing for 24 h, the plates were removed and incubated for a further 48 h, at ambient temperature, and then monitored for growth of the test organism by visual observation.

The following tables provide summary results of three separate studies to determine the minimum amounts of the compounds needed to produce 100% inhibition of growth of the test organism. Results are expressed as minimal volumes (µl/6 L) and amounts (µg/L) required to produce 100% inhibition.

Experiment #1

| Compound # | Compound Name | Concentration (mg compound/ ml ethanol) | Amount for 100% inhibition | |
|---|---|---|---|---|
| | | | (µl of ethanol solution of compound/6 L air) | (µg compound/ L air) |
| 1 | N,2-dimethyl-N-nitrosoisopropanamide | 1.34 | 20 | 4.5 |
| 13 | N-methyl-N-nitrosobutyramide | 1.38 | 40 | 9.2 |
| 7 | N-methyl-N-nitrosocyclopropanecarboxamide | 1.52 | 40 | 10.1 |
| 14 | N-cyclopropyl-N-nitrosoacetamide | 1.39 | 120 | 27.8 |
| 12 | N-nitroso-N-propylacetamide | 1.26 | >120 | 25.2 |
| 16 | N-isopropyl-N-nitrosoacetamide | 1.25 | >120 | 25.0 |

Experiment #2

| Compound # | Chemical Analogue | Concentration (mg compound/ ml ethanol) | Amount for 100% inhibition | |
|---|---|---|---|---|
| | | | (µl of ethanol solution of compound/6 L air) | (µg compound/ L air) |
| 1 | N,2-dimethyl-N-nitrosoisopropanamide | 1.30 | 20 | 4.3 |
| 13 | N-methyl-N-nitrosobutyramide | 4.28 | 10 | 7.1 |
| 7 | N-methyl-N-nitrosocyclopropanecarboxamide | 1.50 | 40 | 10.0 |
| 16 | N-isopropyl-N-nitrosoacetamide | 4.03 | >120 | >80.6 |
| 18 | 1-nitrosopyrrolidin-2-one | 4.20 | >120 | >84.0 |

Experiment #3

| Compound # | Chemical Analogue | Concentration (mg compound/ ml ethanol) | Amount for 100% inhibition | |
|---|---|---|---|---|
| | | | (µl of ethanol solution of compound/6 L) | (µg compound/ L air) |
| 1 | N,2-dimethyl-N-nitrosoisopropanamide | 1.20 | 20 | 4.0 |
| 13 | N-methyl-N-nitrosobutyramide | 1.13 | 40 | 7.5 |
| 7 | N-methyl-N-nitrosocyclopropanecarboxamide | 1.23 | 40 | 8.2 |
| 17 | 1-nitrosopiperidine-2-one | 0.54 | >40 | >3.6 |

Experiment #4

| Compound # | Chemical Analogue | Concentration (mg compound/ ml ethanol) | Amount for 100% inhibition | |
|---|---|---|---|---|
| | | | (µl ethanol solution of compound/6 L air) | (µg compound/ L air) |
| 20 | N-methyl-N-nitrosopropanamide | 1.12 | 40 | 7.5 |
| 2 | N-methyl-N-nitrosohexanamide | 1.28 | 20 | 4.3 |
| 21 | N-methyl-N-nitrosopentanamide | 1.22 | 80 | 16.3 |

-continued

| Compound # | Chemical Analogue | Concentration (mg compound/ ml ethanol) | Amount for 100% inhibition | |
|---|---|---|---|---|
| | | | (μl ethanol solution of compound/6 L air) | (μg compound/ L air) |
| 9 | N-methyl-N-nitrosoheptanamide | 1.12 | 40 | 7.5 |
| 10 | N-methyl-N-nitrosisopropanamide | 1.08 | >80 | >14.4 |
| 1 | N,2-dimethyl-N-nitrosoisopropanamide | 1.26 | 40 | 8.4 |

Experiment #5

| Compound # | Chemical Analogue | Concentration (mg compound/ ml ethanol) | Amount for 100% inhibition | |
|---|---|---|---|---|
| | | | (μl ethanol solution of compound/6 L air) | (μg compound/ L air) |
| 8 | (2E)-N-methyl-N-nitrosobut-2-enamide | 1.13 | 40 | 7.5 |
| 4 | N-methyl-N-nitrosoacrylamide | 1.34 | 5 | 1.1 |
| 22 | N,2-dimethyl-N-nitrosobutanamide | 1.14 | >80 | >15.2 |
| 5 | N-methyl-N-nitrosocyclobutanecarboxamide | 1.43 | 5 | 1.2 |
| 19 | N-3-dimethyl-N-nitrosobutanamide | 1.16 | >80 | >15.5 |

Experiment #6

| Compound # | Chemical Analogue | Concentration (mg compound/ ml ethanol) | Amount for 100% inhibition | |
|---|---|---|---|---|
| | | | (μl ethanol solution of compound/6 L air) | (μg compound/ L air) |
| 6 | 2-methoxy-N-methyl-N-nitrosoacetamide | 1.32 | 10 | 2.2 |
| 3 | 2-cyclopropyl-N-methyl-N-nitrosoacetamide | 1.50 | 20 | 5.0 |
| 15 | Isopropyl-methyl(nitroso)carbamate | 1.15 | 0 | 0 |
| 11 | N-ethyl-N-nitrosoisobutyramide | 1.10 | >80 | >14.7 |
| 18 | N-nitrosopyrolidinone | 1.22 | >80 | >16.3 |
| 17 | N-nitrosopiperidinone | 1.23 | 0 | 0 |

Example 23

Figure 14:
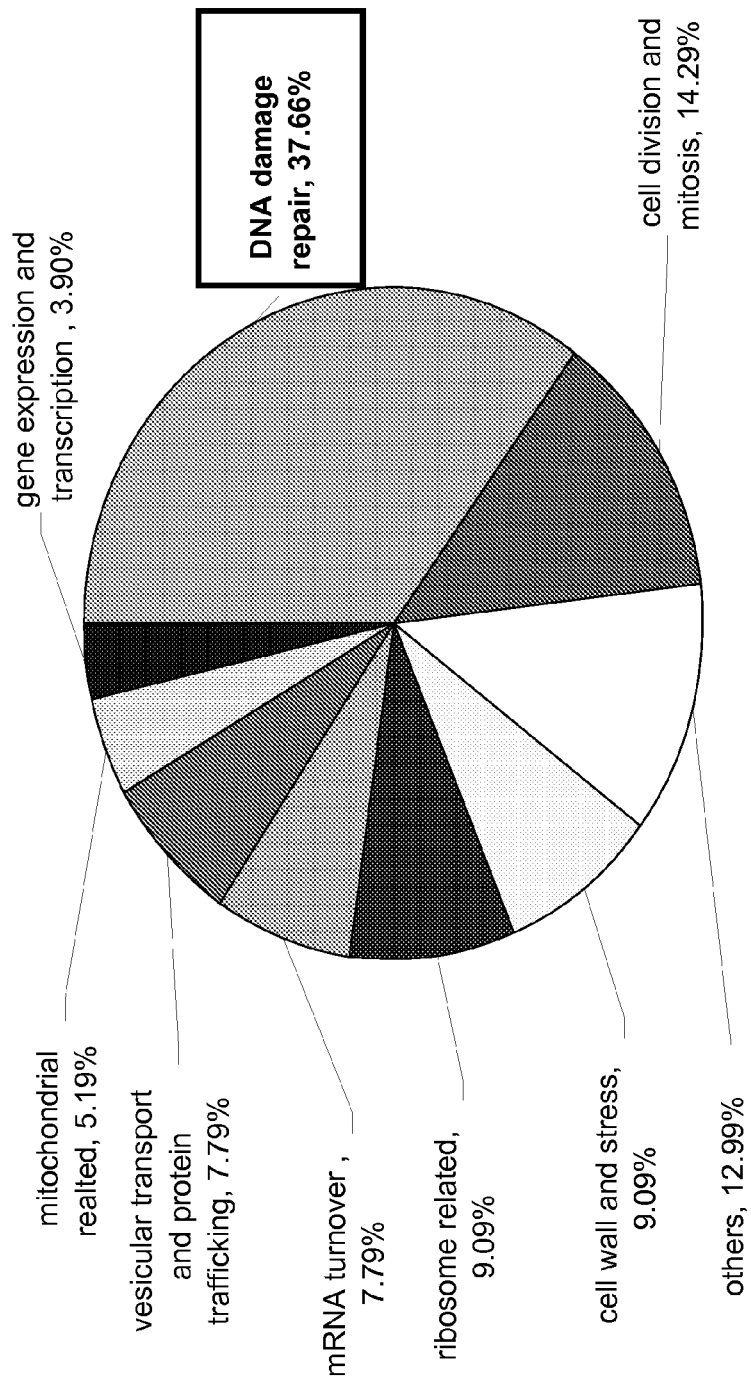
FIG. 14 shows Functional categorization of genes with a role in yeast sensitive to Compound 1.
Figure 15:
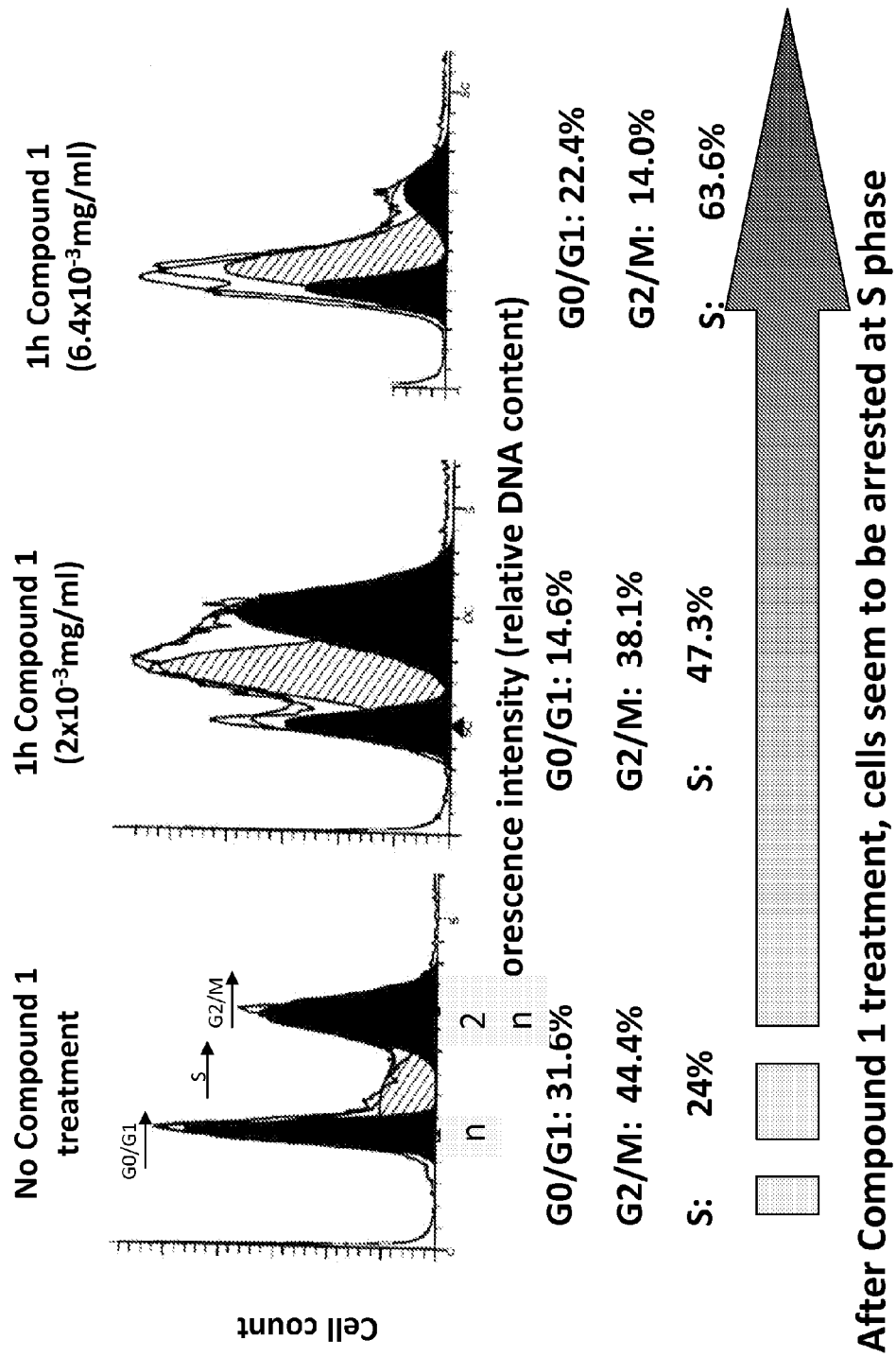
FIG. 15 illustrates a cell cycle study of cells treated with Compound 1.

A study was conducted to determine mode of action of Compound 1 using a high throughput screen of a yeast deletion library. After determining the minimal sub-lethal concentration of compound against yeast cells (15 ug/L air), a high throughput screen was conducted to screen for mutants sensitive to Compound 1 at sub-lethal concentrations. Results are shown in FIGS. 14 and 15. Two 98-well plates in which each well contained a different deletion mutant were either treated with Compound 1 at the sub-lethal concentration of 15 ug/L air or allowed to grow without treatment. Mutants that grew well in the absence of Compound 1 but not in its presence were noted and mutants with sensitivity to Compound 1 were categorized in terms of the nature of their gene deletion, as shown in FIG. 14. About 38% of sensitive mutants were those for which DNA damage repair genes were deleted. Next, the yeast cell cycle was analyzed after Compound 1 treatment. Specifically, yeast cells were grown to log phase and treated with various concentrations of Compound 1 for one hour. The compound was then washed out and the cells grown for another hour, after which the cells were fixed with 70% ethanol and stained with SYBR green stain. Analysis on a flow cytometer indicated that the cell cycle was arrested at S phase, indicating DNA damage which is consistent with a nitrosylating mode of action.

Example 24

A study was performed to evaluate the ability of compounds of the invention to inhibit biofilm formation. Each tested composition was diluted in 10-fold increments into 100% ethanol, which was also used as a vehicle only inoculum in the control biofilm model systems. The dilution values described here represent the inoculated dilutions from the stock test substance (before the final dilutions into 7.5 ml of media or the effects of the 7.5 ml headspace).

*Pseudomonas aeruginosa* PAO1 (ATCC number: BAA-47), *Enterococcus faecalis* V583 (700802) and *Staphylococcus aureus* Mu50 (700699) were maintained in initial cryostock cultures, resuscitated on tryptic soy agar (TSA, Sigma Chemical, St Louis, Mo., US) plates combined with antibiotics to target resistance in each bacterial species. Ampicillin (250 μg/ml) was used for *P. aeruginosa*, vancomycin (40 μg/ml) for *Enterococcus faecalis* and Difco Tellurite Glycine agar (BD & Co., Sparks, Md., US) for *Staphylococcus aureus*. Isolated colonies were inoculated in tryptic soy broth and grown overnight at 37° C. with shaking at 140 revolutions per minute (rpm).

The Lubbock chronic wound biofilm model was utilized for all tests. Chopped meat broth (Oxoid, Hampshire, England) with 48% heparinised bovine plasma and 2% laked blood (HemoStat Laboratories, Dixon, Calif., US) was used as the base biofilm formation media.

7.5 ml biofilm formation media was aseptically dispensed in autoclaved test tubes. Overnight cultures of the bacteria were diluted 100× in trypic soy broth and OD600 measured using a GENESYS-20 spectrophotometer (Thermo Scientific, MA, US).

Plate counts were performed using a Whitley automatic spiral plater (Don Whitley Scientific, MD, US). Bacterial counts were also performed using a modified protocol with the BacLight Viability Kits (Invitrogen, OR, US) for fluorescence microscopy on an Olympus BX51 microscope mounted with an Olympus DP71 digital camera (Olympus Imaging America., Center Valley, Pa., US).

Bacterial count normalised cultures of the bacteria were mixed together (~1×10$^5$ CFU/ml average concentration) and 10 μl of this mixture were inoculated into model system. The tubes with caps sealed were then incubated at 37° C. in a shaker for 24 hours at 140 rpm. Biofilms were evaluated at 24 hours. The headspace was estimated to be 7.5 ml.

DNA extraction was started by placing biofilm samples on dry ice until frozen and then grinding to a homogenous liquid using sterile 15 ml closed tissue grinder systems (FisherScientific, TX, US) connected to a power drill for full homogenisation. 500 μl standard Tris-EDTA pH 7.2 (TE) buffer was added to the tube and vortexed to wash biofilm off the grinder pestle. Samples were transferred to a 1.5 ml Eppendorf tube and 500 μl 0.1 mm glass beads (Scientific Industries, NY, USA) were added for complete bacterial lyses in a Qiagen TissueLyser (QIAGEN, CA, US), run at 30 Hz for five minutes. Samples were centrifuged briefly and 350 μl RLT (with b-ME) and 250 μl 100% ethanol were added to a 100 μl aliquot to prepare samples for DNA extraction.

This solution was added to a DNA spin column and DNA recovery protocols were followed as instructed in the QIAamp DNA Mini Kit (QIAGEN, CA, USA) starting at step 7 of the tissue protocol. DNA was eluted from the column with 100 μl water and samples were diluted accordingly to a final concentration of 20 ng/μl for use with SYBR Green based quantitative PCR. SYBR Green is a dye that intercalates with double-stranded DNA, and this intercalation causes the SYBR to fluoresce allowing quantification of DNA based upon the relative amount of fluorescence detected.

Quantitative PCR (qPCR) was used to evaluate the relative ratios of each bacterium using the Roche 480 instrument. Primers for each bacterial species, along with Bio-Rad iTaq SYBR-Green Supermix with ROX, was used for 25 μl real-time qPCR reactions as follows: 95° C. for 10 minutes, and 40 cycles of 95° C. for 15 seconds and 60° C. for 60 seconds. All reactions were performed in triplicate. The relative genome copy number ratios were calculated and analysed (User Bulletin #2, ABI PRISM 7700 Sequence Detection System). In brief, the threshold cycle (Ct value) of the target genes in different samples was obtained after qPCR reaction. The Ct value of the calibrator (the sample with the highest Ct value) was subtracted from every other sample to produce the ddCt value. Two to the -ddCt power (2-ddCt) was taken for every sample and used to evaluate relative ratios of each bacteria.

Table 4 describes the results of the biofilm inhibition study. A 1:10 dilution of the test substance inoculated into the 15 ml test system (7.5 ml liquid, 7.5 ml headspace) was effective at prevention of biofilm. The higher dilutions (1:100 up to 1:10, 000) also showed moderate to high inhibition of biofilm formation. These results were further supported by the dry weight analysis of biofilm formation.

TABLE 4

Biofilm inhibition experiments.

| Treatment | biofilm formation | dry weight mg ± SD | P. aeruginosa | E. faecalis | S. aureus |
|---|---|---|---|---|---|
| Untreated Control | ++++ | 96.3 ± 5.9 | 15.8% ± 1.1% | 35.2% ± 1.4% | 48.9% ± 0.7% |
| Compound 1 (1:10000) | +++ | 79.7 ± 5.5 | 20.3% ± 0.9% | 32.6% ± 0.3% | 47.2% ± 1.2% |
| Compound 1 (1:1000) | ++ | 63 ± 5.3 | 50.5% ± 8.4% | 34.4% ± 0.2% | 15.2% ± 1.6% |
| Compound 1 (1:100) | + | 59 ± 4.4 | 46.7% ± 8.0% | 39.5% ± 1.0% | 13.9% ± 0.2% |
| E1 (1:10) | ± | 21.7 ± 3.2 | 34.3% ± 1.2% | 65.5% ± 0.6% | 0.27% ± 0.0% |

As shown in table 4, compound 1 had an increased impact on the MRSA strain of *Staphylococcus aureus* which was concentration dependent and a trend effect on *Pseudomonas aeruginosa* to be inhibited in comparison to *Enterococcus faecalis*.

Example 25

Compound 1 was evaluated to determine the Minimum Inhibitory Concentration (MIC) and Minimum Bactericidal Concentration (MBC) Test by Macrodilution Broth Method.

The following microorganisms were tested in this assay: *Corynebacterium renale* (ATCC 10848), *Klebsiella pneumoniae* (ATCC 35657), *Proteus mirabilis* (ATCC 3559), *Enterobacter cloacae* (ATCC 13047), *Clostridium sporogenes* (ATCC 11437), *Legionella pneumophila* (ATCC 33152), *Streptococcus pyogenes* (ATCC 10096), Methicillin Resistant *Staphylococcus aureus* (MRSA) (ATCC 33591), *E. coli* 0157:H7 (ATCC 43894), *Shigella dysenteriae* (ATCC 12021), *Bacillus cereus* (ATCC 10702), and *Listeria monocytogenes* (ATCC 13932).

Each organism's inoculums was prepared by streaking agar plates (TSA for bacteria, except *Clostridium*, and SDA for fungi). The plates were incubated at 30-35° C. for 18-24 hrs for bacteria (24-48 hours for *Bacillus*) and at 20-25° C. and NLT 3 days for fungi. For *Clostridium* strains the suspension was prepared by adding 100 g of ground beef, 500 ml of sterile waster and 5 mg of magnesium sulfate. This preparation was then autoclaved @121° C. for 25 minutes. 1 ml of *Clostrium sporogenes* stock suspension of the organism was then added to suspension and incubated at 37° C. for 72 hours. A plate count was then performed on ISA media and incubated anaerobically at 30-35° C. The organisms suspensions were prepared with a target concentration of $>1 \times 10^8$ CFU/mL for bacteria and $>1 \times 10^7$ for Yeast by inoculating diluent with the fresh culture. After the suspensions were prepared, they were enumerated by making 10-fold serial dilutions and plated onto appropriate media to ensure that the concentration was within target.

Media was prepared from a dehydrated base as recommended by manufacturer. FTM broth was used to test *Clostridium sporogenes*. All other organisms used the M-H broth. 12 tubes were prepared with 1 ml of media broth for each organism to be tested. The last two tubes were used as controls (positive and negative). Tubes 1 to 10 were used for the MIC test. Each organism was tested in triplicate. 1 mL of the prepared 100 ppm test solution was added to the first broth tube and vortexed. From there, 2-fold dilutions were performed by transferring 1 mL from tube 1 to tube 2, then tube 2 was then diluted to tube 3 and this process was continued through tube 10. Tube 11 contained no antimicrobial (positive control) and tube 12 was broth only (negative control).

The inoculum suspensions were diluted from approximately $1 \times 10^8$ CFU/ml to $1 \times 10^6$ CFU/ml, so that after inoculation each macrodilution tube contained approximately $2 \times 10^5$ CFU/mL. Within 15 minutes after the inoculum has been standardized as described above, 1 ml of the adjusted inoculum was added to each tube already containing 1 mL of antimicrobial agent and broth in the dilution series tubes. This was also done for the positive control. Each tube was then mixed and this resulted in a 1:1 dilution of each antimicrobial concentration. The dilution of the inoculum had been diluted from approximately $1 \times 10^6$ CFU/ml to approximately $5 \times 10^5$ CFU/mL, since 1 mL of suspension is inoculated into 1 ml of broth. Tube 12 (un-inoculated tube) of broth, was incubated to be used as the negative control. The macrodilution tubes were incubated at 37° C. for 16 to 20 hours. After the incubation period, the MIC dilution end points were calculated. The first tube had a concentration of 50 ppm, second tube 25 ppm, and so on.

The MIC is the lowest concentration of antimicrobial agent that completely inhibits growth of the organism in the broth tubes. The amount of growth on the tubes with antimicrobial was compared with the amount of growth in the positive control tubes (no compound) used in each sets of test when determining the growth end points.

After the MIC test was completed, the broth dilution tubes that had no growth from the MIC test were subcultured onto M-H agar plates. The positive control was subcultured from the MIC broth. All the subcultured plates were incubated at 37° C. for 16-20 hours. *Clostridium* plates were incubated anaerobically. The MBC is the lowest concentration of antimicrobial agent that kills the organism completely in the tube. The dilution tubes from the MIC that showed no growth were plated on media to determine the MBC. This was calculated based on the lowest concentration without any growth observed on the subcultured plates.

Results for the MIC and MBC are shown in Table 5. The growth of most microorganisms was inhibited by a test compound concentration of 12.5 ppm.

TABLE 5

Minimum Inhibitory Concentration and Minimum Bactericidal Concentration Test Results

| Organism | MIC concentration (ppm) | MBC concentration (ppm) | Diluted Suspension Concentration (CFU/ml) | Final Concentration after inoculation (CFU/ml) |
|---|---|---|---|---|
| *Enterobacter cloacae* | 12.5 | 12.5 | $3.7 \times 10^5$ | $1.9 \times 10^5$ |
| *Escherichia coli* 0157:H7 | 12.5 | 12.5 | $6.1 \times 10^5$ | $3.1 \times 10^5$ |
| *Listeria monocytogenes* | 3.13 | 12.5 | $8.8 \times 10^5$ | $4.4 \times 10^5$ |
| *Proteus mirabilis* | 6.25 | 12.5 | $4.8 \times 10^5$ | $2.4 \times 10^5$ |
| *Klebsiella pneumoniae* | 12.5 | 12.5 | $3.7 \times 10^5$ | $1.9 \times 10^5$ |
| *Legionella pneumophila* | 6.25 | 25 | $6.7 \times 10^5$ | $3.4 \times 10^5$ |
| *Shigella dysenteriae* | 6.25 | 12.5 | $3.7 \times 10^5$ | $1.9 \times 10^5$ |
| Methycillin Resistant *Staphylococcus aureus* | 6.25 | 12.5 | $1.9 \times 10^5$ | $9.5 \times 10^4$ |
| *Bacillus cereus* | 6.25 | 12.5 | $2.7 \times 10^5$ | $1.4 \times 10^5$ |
| *Streptococcus pyrogenes* | 6.25 | 6.25 | $2.7 \times 10^5$ | $1.4 \times 10^5$ |
| *Corynebacterum renale* | 6.25 | 12.5 | $9.8 \times 10^4$ | $4.9 \times 10^4$ |
| *Clostridium sporogenes* | 25 | N/A[1] | $3.1 \times 10^6$ | $1.6 \times 10^6$ |

[1]Growth was observed on all the plates (50 ppb was highest concentration plated)

Example 26

Compound 1 and 6 analogs of Compound 1 were evaluated to determine the Minimum Inhibitory Concentration (MIC) and Minimum Bactericidal Concentration (MBC).

*Staphylococcus aureus* (MRSA) (ATCC 33591) inoculums were prepared by streaking 4 TSA plates. The plates were incubated at 30-35° C. for 23 hrs. The organism suspension was prepared with a target concentration of $>1 \times 10^8$ CFU/mL by inoculating diluent with the fresh culture. After the suspension was prepared, it was enumerated by making 10-fold serial dilutions, plated onto TSA media to ensure that the concentration was within target.

Media was prepared from a dehydrated base as recommended by the manufacturer and augmented by the addition of magnesium and calcium stock solutions. 1000 ppm solutions of each compound tested were prepared.

Eleven (11) tubes were prepared with 1 ml of MR Broth. Tubes 1 to 9 were used for the MIC test. Tubes 11 and 21 were used as controls (positive and negative). 200 µL of the prepared 1000 ppm compound solutions was added to the first broth tube and vortexed with the cap on. 2-fold dilutions were performed by transferring 1 mL from tube 1 to tube 2 and so on to tube 9. For each compound, the test was performed in triplicate. An additional series of 1:1 dilutions were performed with pure ethanol and used as a control.

The inoculum suspensions were diluted from approximately $1 \times 10^8$ CFU/ml to $1 \times 10^6$ CFU/ml, so that after inoculation each macrodilution tube contained approximately $5 \times 10^5$ CFU/mL. Within 15 minutes after the inoculum has been standardized as described above, 1 ml of the adjusted inoculum was added to each tube already containing 1 mL of antimicrobial agent and broth in the dilution series tubes. This was also done for the positive control. Each tube was then mixed and this resulted in a 1:1 dilution of each antimicrobial concentration. The dilution of the inoculum had been diluted from approximately $1 \times 10^{10}$ CFU/ml to approximately $5 \times 10^5$ CFU/mL, since 1 mL of suspension is inoculated into 1 ml of broth. The un-inoculated tube (Tube 11) was used as the negative control. The macrodilution tubes were incubated at $37 \pm 1°$ C. for 19 hours. After the incubation period, the MIC dilution end points were calculated. The first tube had a concentration of 50 ppm, second tube 25 ppm, and so on.

The MIC is the lowest concentration of anti microbial agent that completely inhibits growth of the organism in the broth tubes. The amount of growth on the tubes with antimicrobial was compared with the amount of growth in the positive control tubes (no compound) used in each sets of test when determining the growth end points. After the MIC test was completed, the broth dilution tubes that had no growth from the MIC test were subcultured onto M-H Agar plates. The positive control was also subcultured from the MIC broth. The subcultured plates were incubated at $37 \pm 1°$ C. for 25 hours.

The MBC is the lowest concentration of antimicrobial agent that kills the organism completely in the tube. The dilution tubes from the MIC that showed no growth were plated on media to determine the MBC. This was determined based on the lowest concentration without any growth observed on the subcultured plates.

The results for the MIC and MBC are shown in Table 6.

TABLE 6

MIC Summary Results for MA130 and analogs

| Compound Structure | MIC (ppm) | MBC (ppm) |
|---|---|---|
| Compound No. 1 | 6.25 | 12.5 |
| (H3CO-CH2-C(=O)-N(CH3)-NO) | 25 | >50[1] |
| (CH2=CH-C(=O)-N(CH3)-NO) | >50[1] | >50[1] |
| (CH3-CH=CH-C(=O)-N(CH3)-NO) | 6.25 | 25 |
| (CH3CH2-C(=O)-N(CH3)-NO) | 12.5 | 25 |
| (hexanoyl-N(CH3)-NO) | 6.25 | 25 |
| (isovaleryl-N(CH3)-NO) | 0.78 | 25 |
| Pure Ethanol Blank Control | >50[1] | N/A |

[1]Growth was observed in all tubes or on all plates (50 ppm = highest concentration used)

What is claimed is:

1. A method of controlling the growth of microorganisms on a material after the first occurrence selected form the group consisting of a foodstuff, soil, a building material, a medical or veterinary tool, and a seed comprising applying to the material a composition comprising an isolated or in vitro synthesized compound of Formula 2:

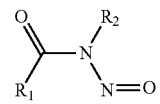

Formula 2 wherein $R_1$ is an alkyl, haloalkyl, cycloalkyl, alkenyl, haloalkenyl or cycloalkenyl group and $R_2$ is a methyl group.

2. The method of claim 1, wherein $R_1$ is a $C_1$-$C_6$ alkyl group.

3. The method of claim 1, wherein $R_1$ is an alkenyl group.

4. The method of claim 1, wherein the applying is carried out by fumigating.

5. The method of claim 1, wherein the material is a foodstuff.

6. The method of claim 1, wherein the material is soil.

7. The method of claim 1, where the material is a building material.

8. The method of claim 1, where the material is a medical or veterinary tool.

9. The method of claim 1, where the material is a seed.

10. The method of claim 1, wherein the microorganisms are selected from the group consisting of *Rhizoctonia solani, Pythium ultimum, Fusarium, Verticiliium dahliae* and *Penicillium expansum*.

11. The method of claim 1 wherein the microorganisms are food-borne pathogens.

* * * * *